US010183899B2

(12) United States Patent
Bischof

(10) Patent No.: US 10,183,899 B2
(45) Date of Patent: Jan. 22, 2019

(54) NORMAL ALPHA OLEFIN SYNTHESIS USING METATHESIS AND DEHYDROFORMYLATION

(71) Applicant: Chevron Phillips Chemical Company LP, The Woodlands, TX (US)

(72) Inventor: Steven M. Bischof, Humble, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 44 days.

(21) Appl. No.: 15/347,833

(22) Filed: Nov. 10, 2016

(65) Prior Publication Data

US 2018/0127329 A1 May 10, 2018

(51) Int. Cl.
*C07C 1/207* (2006.01)
*C07C 45/50* (2006.01)
*C07C 6/04* (2006.01)

(52) U.S. Cl.
CPC .............. *C07C 1/2076* (2013.01); *C07C 6/04* (2013.01); *C07C 45/50* (2013.01); *C07C 2531/22* (2013.01)

(58) Field of Classification Search
None
See application file for complete search history.

(56) References Cited

U.S. PATENT DOCUMENTS

| 4,272,444 | A | 6/1981 | McCombs et al. | |
|---|---|---|---|---|
| 8,765,984 | B2 | 7/2014 | Upshaw | |
| 9,115,069 | B2 | 8/2015 | Papp et al. | |
| 2002/0193650 | A1* | 12/2002 | Goze | C08F 8/04 585/521 |
| 2013/0274482 | A1* | 10/2013 | Schrock | B01J 31/1805 548/402 |

FOREIGN PATENT DOCUMENTS

| CA | 1048533 | 2/1979 |
|---|---|---|
| WO | WO 2001/00546 | 1/2001 |
| WO | WO 2001/05735 | 1/2001 |
| WO | WO 2014/088800 | 6/2014 |
| WO | WO 2015/094813 | 6/2015 |

OTHER PUBLICATIONS

Pandey et al. "Terminal Olefins from Aldehydes through Enol Triflate Reduction", J. Org. Chem. 2007, 72, p. 7769-7770.*

Selent et al. "New Phosphorus Ligands for the Rhodium-Catalyzed Isomerization/Hydroformylation of Internal Octenes", Angew. Chem. Int. Ed. 2001, 40, No. 9, p. 1696-1697.*
Murphy et al. "Rh-catalyzed C—C bond cleavage by transfer hydroformylation", Science, Research Reports, vol. 347, Issue 6217, p. 56-59, Jan. 2, 2015.*
Luo et al., "Mechanism of Rhodium-Catalyzed Formyl Activation: A Computational Study", J. Org. Chem., 81, 2320-2326. (Year: 2016).*
Murphy et al., "Rh-catalyzed C—C bond cleavage by transfer hydroformylation"; Science, vol. 347, Issue 6217, p. 56-60 (Year: 2015).*
Chatterjee et al., entitled "*A General Model for Selectivity in Olefin Cross Metathesis,*" J. Am. Chem. Soc. (2003), vol. 125, pp. 11360-11370.
Chatterjee et al., entitled "*A General Model for Selectivity in Olefin Cross Metathesis,*" J. Am. Chem. Soc. (2003), Supporting Info., pp. S1-S27.
Haymore et al., entitled "*Regioselectivity in Hydroformylation of Linear and Branched Octenes Using HCo(CO)$_4$,*" Annals NY Academy of Sciences (1983), vol. 415, pp. 159-175.
Keim, entitled, "*Oligomerization of Ethylene to α-Olefins: Discovery and Development of the Shell Higher Olefin Process (SHOP),*" Angew. Chem. Int. Ed. (2013), vol. 52, pp. 12492-12496.
Murphy et al., entitled "*Rh-catalyzed C—C bond cleavage by transfer hydroformylation,*" Science (2014), Supporting Info., vol. 347, Issue 56, pp. S1-S71.
Murphy et al., entitled "*Rh-catalyzed C—C bond cleavage by transfer hydroformylatzon,*" Science (2015), vol. 347, Issue 6217, pp. 56-60.
Selent et al., entitled "*New Phosphorus Ligands for the Rhodium-Catalyzed Isomerization/Hydroformylation of Internal Octenes,*" Angew. Chem. Int. Ed. (2001), vol. 40, No. 9, pp. 1696-1698.
Thomas et al., entitled "*Highly Selective Ruthenium Metathesis Catalysts for Ethenolysis,*" J. Am. Chem. Soc. (2011), vol. 133, pp. 7490-7496.
Thomas et al., entitled "*Highly Selective Ruthenium Metathesis Catalysts for Ethenolysis,*" J. Am. Chem. Soc. (2011), Supporting Info, pp. S1-S32.

* cited by examiner

Primary Examiner — In Suk C Bullock
Assistant Examiner — Ali Z Fadhel
(74) Attorney, Agent, or Firm — Merchant & Gould, P.C.

(57) ABSTRACT

The present invention discloses processes for producing normal alpha olefins, such as 1-hexene, 1-octene, and 1-decene, in a multistep synthesis scheme. Generally, a first normal alpha olefin is subjected to an olefin metathesis step to form a linear internal olefin, which is then subjected to an isomerization-hydroformylation step to form a linear aldehyde, which is then subjected to a dehydroformylation step to form a second normal alpha olefin.

20 Claims, No Drawings

NORMAL ALPHA OLEFIN SYNTHESIS USING METATHESIS AND DEHYDROFORMYLATION

BACKGROUND OF THE INVENTION

The present invention relates generally to processes for producing normal alpha olefins in a multistep synthesis scheme that can include an olefin metathesis step, a hydroformylation step, and a dehydroformylation step.

SUMMARY OF THE INVENTION

This summary is provided to introduce a selection of concepts in a simplified form that are further described herein. This summary is not intended to identify required or essential features of the claimed subject matter. Nor is this summary intended to be used to limit the scope of the claimed subject matter.

Processes for producing normal alpha olefins are disclosed and described herein. One such process can comprise (i) contacting a first normal alpha olefin having the structure $CH_3(CH_2)_nHC=CH_2$ and a metathesis catalyst system to form a linear internal olefin having the structure $CH_3(CH_2)_nHC=CH(CH_2)_nCH_3$; (ii) contacting the linear internal olefin with a hydroformylation catalyst system, carbon monoxide, and hydrogen to form a linear aldehyde having the formula $CH_3(CH_2)_{2n+3}C(=O)H$; and (iii) contacting the linear aldehyde with a dehydroformylation catalyst system comprising i) a transition metal compound, a diphosphine, and a carboxylic acid or carboxylic acid derivative, or ii) a diphosphine transition metal compound complex and a carboxylic acid or carboxylic acid derivative, to form a second normal alpha olefin having the structure $CH_3(CH_2)_{2n+1}HC=CH_2$. In this process, n is an integer that can range from 0 to 15.

Another process for producing normal alpha olefins consistent with embodiments of this invention can comprise (a) contacting a linear internal olefin having the structure $CH_3(CH_2)_pHC=CH(CH_2)_qCH_3$ with a hydroformylation catalyst system, carbon monoxide, and hydrogen to form a linear aldehyde having the formula $CH_3(CH_2)_{p+q+3}(=O)H$; and (b) contacting the linear aldehyde with a dehydroformylation catalyst system comprising i) a transition metal compound, a diphosphine, and a carboxylic acid or carboxylic acid derivative, or ii) a diphosphine transition metal compound complex and a carboxylic acid or carboxylic acid derivative, to form a normal alpha olefin having the structure $CH_3(CH_2)_{p+q+1}HC=CH_2$. In this process, p and q can be integers that independently range from 0 to 15. Therefore, p and q can be the same or different; alternatively, p and q can be the same; or alternatively, p and q can be different. In some embodiments, the linear internal olefin having the structure $CH_3(CH_2)_pHC=CH(CH_2)_qCH_3$ can be produced by contacting a normal alpha olefin having the formula $CH_3(CH_2)_pHC=CH_2$, a normal alpha olefin having the formula $CH_3(CH_2)_qHC=CH_2$, and a metathesis catalyst system to form a linear internal olefin having the structure $CH_3(CH_2)_pHC=CH(CH_2)_qCH_3$; e.g., the process for producing the normal alpha olefin can further comprise a step of contacting a normal alpha olefin having the structure $CH_3(CH_2)_pHC=CH_2$, a normal alpha olefin having the formula $CH_3(CH_2)_qHC=CH_2$, and a metathesis catalyst system to form the linear internal olefin having the structure $CH_3(CH_2)_pHC=CH(CH_2)_qCH_3$.

In step (iii) and step (b) of these processes, the linear aldehyde can be contacted with 1) the dehydroformylation catalyst system comprising i) the transition metal compound, the diphosphine, and the carboxylic acid or carboxylic acid derivative, or ii) the diphosphine transition metal compound complex and the carboxylic acid or carboxylic acid derivative, and 2) an aldehyde group acceptor to form the respective normal alpha olefin.

Both the foregoing summary and the following detailed description provide examples and are explanatory only. Accordingly, the foregoing summary and the following detailed description should not be considered to be restrictive. Further, features or variations can be provided in addition to those set forth herein. For example, certain aspects and embodiments can be directed to various feature combinations and sub-combinations described in the detailed description.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects and/or embodiments, a combination of different features can be envisioned. For each and every aspect, and/or embodiment, and/or feature disclosed herein, all combinations that do not detrimentally affect the designs, compositions, processes, and/or methods described herein are contemplated with or without explicit description of the particular combination. Additionally, unless explicitly recited otherwise, any aspect, and/or embodiment, and/or feature disclosed herein can be combined to describe inventive features consistent with the present disclosure.

Regarding claim transitional terms or phrases, the transitional term "comprising," which is synonymous with "including," "containing," "having," or "characterized by," is open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristics of the claimed invention. A "consisting essentially of" claim occupies a middle ground between closed claims that are written in a "consisting of" format and fully open claims that are drafted in a "comprising" format. Absent an indication to the contrary, describing a composition or method as "consisting essentially of" is not to be construed as "comprising," but is intended to describe the recited element that includes materials or steps which do not significantly alter the composition or method to which the term is applied. For example, an olefin feedstock consisting essentially of a material A can include impurities typically present in a commercially produced or commercially available sample of the recited compound or composition. When a claim includes different features and/or feature classes (for example, a method step, olefin feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize an olefin feedstock consisting of specific components; alternatively, consisting essentially of specific components; or alternatively, comprising the specific components and other non-recited components. While compositions and methods are described in terms of "comprising" various components or steps, the compositions and methods can also "consist essentially of" or "consist of" the various components or steps, unless specifically stated otherwise.

The terms "a," "an," and "the" are intended to include plural alternatives, e.g., at least one, unless otherwise specified. For instance, the disclosure of "a normal alpha olefin" or "an acceptor olefin" is meant to encompass one, or combinations of more than one, normal alpha olefin or acceptor olefin, respectively, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; a general reference to a butyl group includes an n-butyl group, a sec-butyl group, an iso-butyl group, and a t-butyl group; and a general reference to cyclododecatriene includes all isomeric forms (e.g., trans,trans,cis-1,5,9-cyclododecatriene, and trans,trans,trans-1,5,9-cyclododecatriene, among other dodecatrienes).

The terms "contact product," "contacting," and the like, are used herein to describe compositions and methods wherein the components are contacted or combined together in any order, in any manner, and for any length of time, unless otherwise specified. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, the term "contacting" is used herein to refer to materials which can be blended, mixed, slurried, dissolved, reacted, treated, or otherwise contacted in some other manner. Hence, "contacting" two or more components can result in a mixture, a reaction product, a reaction mixture, etc.

The term "hydrocarbon" whenever used in this specification and claims refers to a compound containing only carbon and hydrogen. The term "olefin" as used herein refers to a hydrocarbon that has at least one carbon-carbon double bond that is not part of an aromatic ring or ring system. The term "olefin" includes aliphatic and aromatic, cyclic and acyclic, and/or linear and branched compounds having at least one carbon-carbon double bond that is not part of an aromatic ring or ring system, unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s). The term "alpha olefin" as used herein refers to any olefin that has a double bond between the first and second carbon atom of a contiguous chain of carbon atoms. The term "alpha olefin" includes linear and branched alpha olefins and alpha olefins which can have more than one non-aromatic carbon-carbon double bond, unless expressly stated otherwise.

The term "normal alpha olefin" as used herein refers to a linear aliphatic hydrocarbon mono-olefin having a double bond between the first and second carbon atom. The term "linear internal olefin" as used herein refers to a linear aliphatic hydrocarbon mono-olefin having a double bond that is not between the first and second carbon atom, can be further described by the chemical formulas provided throughout this disclosure.

An "aromatic compound" refers to a compound containing a cyclically conjugated moiety that follows the Hückel (4n+2) rule and containing (4n+2) pi-electrons, where n is an integer from 1 to about 5. Aromatic compounds can be monocyclic or polycyclic, unless otherwise specified. Non-limiting examples of aromatic compounds include benzene, naphthalene, and toluene, among others.

As utilized herein, the term "solvent" applies to a material which can dissolve a compound or a material which can dilute the components of a reaction. As such, the term "solvent" can be inferred to encompass materials which can act as a solvent and/or a diluent, unless expressly stated otherwise.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Processes for producing normal alpha olefins are disclosed herein. Beneficially, the disclosed processes do not add an extra carbon atom to traditional olefin metathesis products, such that even number carbon atom normal alpha olefins can be converted into larger even number carbon atom normal alpha olefins. Illustrative examples can include, but are not limited to, the synthesis of 1-hexene from 1-butene, and the synthesis of 1-decene from 1-hexene.

Normal Alpha Olefin Synthesis

Embodiments of this invention are directed to processes for producing normal alpha olefins. One such process can comprise (or consist essentially of, or consist of) (i) contacting a first normal alpha olefin having the structure $CH_3(CH_2)_nHC=CH_2$ and a metathesis catalyst system to form a linear internal olefin having the structure $CH_3(CH_2)_n HC=CH(CH_2)_nCH_3$; (ii) contacting the linear internal olefin with a hydroformylation catalyst system, carbon monoxide, and hydrogen to form a linear aldehyde having the formula $CH_3(CH_2)_{2n+3}C(=O)H$; and (iii) contacting the linear aldehyde with a dehydroformylation catalyst system comprising i) a transition metal compound, a diphosphine, and a carboxylic acid or carboxylic acid derivative, or ii) a diphosphine transition metal compound complex and a carboxylic acid or carboxylic acid derivative, to form a second normal alpha olefin having the structure $CH_3 (CH_2)_{2n+1}HC=CH_2$. In this process, n can be an integer that can range from 0 to 15. Generally, the features of this process (e.g., the first normal alpha olefin, the metathesis catalyst, the linear internal olefin, the hydroformylation catalyst system, the linear aldehyde, the dehydroformylation catalyst system, the second normal olefin, and the conditions under which each of the steps are conducted, among other features) are independently described herein and these features can be combined in any combination to further describe the disclosed normal alpha olefin synthesis processes. Moreover, additional process steps can be performed before, during, and/or after any of the steps of any of the processes disclosed herein, unless stated otherwise.

As described herein, n can be an integer that can range from 0 to 15. In one embodiment consistent with this invention, n can be an integer from 0 to 10, while in another embodiment, n can be an integer from 0 to 7. Yet, in another embodiment, n can be an integer from 1 to 7, and in still another embodiment, n can be an integer from 1 to 5. For example, n can be equal to 1, equal to 2, equal to 3, equal to 4, and so forth.

In some embodiments of this invention, the first normal alpha olefin can comprise, consist essentially of, or consist of, propylene, 1-butene, 1-pentene, 1-hexene, 1-heptene, 1-octene, 1-nonene, 1-decene, 1-dodecene, 1-tetradecene, 1-hexadecene, 1-octadecene, or any combination thereof; alternatively, 1-butene, 1-pentene, 1-hexene, 1-heptene, 1-octene, or any combination thereof; or alternatively, 1-butene, 1-pentene, 1-hexene, or any combination thereof. In further embodiments, the first normal alpha olefin can comprise, consist essentially of, or consist of, propylene; alternatively, 1-butene; alternatively, 1-pentene; alternatively, 1-hexene; alternatively, 1-heptene; alternatively, 1-octene; alternatively, 1-nonene; alternatively, 1-decene; alternatively, 1-dodecene; alternatively, 1-tetradecene; alternatively, 1-hexadecene; or alternatively, 1-octadecene.

In one embodiment of this invention, the first normal alpha olefin can comprise (or consist essentially of, or consist of) 1-butene, and the second normal alpha olefin can comprise (or consist essentially of, or consist of) 1-hexene. In another embodiment of this invention, the first normal alpha olefin can comprise (or consist essentially of, or consist of) 1-pentene, and the second normal alpha olefin can comprise (or consist essentially of, or consist of) 1-octene. In yet another embodiment of this invention, the first normal alpha olefin can comprise (or consist essentially of, or consist of) 1-hexene, and the second normal alpha olefin can comprise (or consist essentially of, or consist of) 1-decene.

The integer n, the first normal alpha olefin, and the second normal alpha olefin are described herein and their features can be utilized without limitation to further describe the normal alpha olefin synthesis processes disclosed herein. Other suitable values for the integer n and selections for the first normal alpha olefin and the second normal alpha olefin are readily apparent from this disclosure.

Step (i) of the processes disclosed herein often is referred to as the metathesis step, and in this step, the first normal alpha olefin having the structure $CH_3(CH_2)_nHC=CH_2$ can be contacted with a metathesis catalyst system to form a linear internal olefin having the structure $CH_3(CH_2)_n HC=CH(CH_2)_nCH_3$.

Any suitable metathesis catalyst system can be used in the metathesis step, non-limiting examples of which can include a metal oxide based metathesis catalyst system, a metal halide based metathesis catalyst system, a metal carbene based metathesis catalyst system, or any combination thereof. In one embodiment, the metathesis catalyst system can be a metal oxide based metathesis catalyst system or a metal halide based metathesis catalyst system, while in another embodiment, the metathesis system catalyst can be a metal oxide based metathesis catalyst system; alternatively, a metal halide based metathesis catalyst system; or alternatively, a metal carbene based metathesis catalyst system.

Metal oxide based metathesis catalyst systems can comprise (or consist essentially of, or consist of) cobalt oxide, molybdenum oxide, tungsten oxide, rhenium oxide, or any combination thereof. For instance, the metal oxide based catalyst system can comprise (or consist essentially of, or consist of) cobalt oxide; alternatively, molybdenum oxide; alternatively, tungsten oxide; or alternatively, rhenium oxide. Optionally, the metal oxide based metathesis catalyst system can further comprise a support, or a metal alkyl activator, or both a support and a metal alkyl activator. Illustrative supports can include alumina, silica, silica-alumina, and aluminum-phosphate, amongst other solid oxide materials. Accordingly, non-limiting examples of supported metal oxide based metathesis catalyst systems can include molybdenum oxide on alumina ($MoO_3/Al_2O_3$), tungsten oxide on silica ($WO_3/SiO_2$), rhenium oxide on alumina ($Re_2O_7/Al_2O_3$), cobalt oxide and molybdenum oxide on alumina ($CoO/MoO_3/Al_2O_3$), and rhenium oxide on alumina activated with tetramethyl tin ($Re_2O_7/Al_2O_3/SnMe_4$). Other suitable metal oxide based metathesis catalyst systems are known to those skilled in the art.

Further, the metal oxide based metathesis catalyst system can include a metal alkyl activator, which can include alkyl lithium, alkyl magnesium, alkyl aluminum, alkyl tin compounds, or any mixture thereof. In an embodiment, the metal alkyl activator can be an alkyl lithium compound. In another embodiment, the metal alkyl activator can be an alkyl magnesium compound. In another embodiment, the metal alkyl activator can be an alkyl aluminum compound. In yet another embodiment, the metal alkyl activator can be an alkyl tin compound. Non-limiting examples of alkyl aluminum compounds can include trialkyl aluminum compounds and/or alkyl aluminum halide compounds. The alkyl groups on the metal alkyl activator can include any $C_1$ to $C_{10}$ hydrocarbyl group, or alternatively, any $C_1$ to $C_5$ hydrocarbyl group. In various embodiments, the alkyl group for the metal alkyl activator can be a methyl group, ethyl group, n-propyl group, iso-propyl group, n-butyl group, sec-butyl group, or tert-butyl group; alternatively, a methyl group, ethyl group, n-butyl group, sec-butyl group, or tert-butyl group; alternatively, a methyl group; alternatively, an ethyl group; alternatively, an n-butyl group; alternatively, a sec-butyl group; or alternatively, a tert-butyl group. Representative examples of suitable trialkyl aluminum compounds can include trimethylaluminum, triethylaluminum, and triisobutylaluminum. The halide of the alkyl aluminum halide compound can be chloride, bromide, or iodide; alternatively, chloride; alternatively, bromide; or alternatively, iodide. Examples of suitable alkyl aluminum halide compounds can include ethylaluminum dichloride, diethylaluminum chloride, and ethylaluminum sesquichloride. Suitable and non-limiting examples of alkyl tin compounds can include tetramethyl tin, tetraethyl tin, and tetrabutyl tin.

Metal halide based metathesis catalyst systems can comprise (or consist essentially of, or consist of) a halide of tungsten, a halide of molybdenum, or a combination thereof. For instance, the metal halide based metathesis catalyst system can comprise (or consist essentially of, or consist of) a halide of tungsten, or alternatively, a halide of molybdenum. The halide of the metal halide based metathesis catalyst system can be chloride, bromide, or iodide. In one embodiment, the halide can be chloride, and in another embodiment, the halide can be bromide, and in yet another embodiment, the halide can be iodide. Hence, the metal halide based metathesis catalyst system can comprise (or consist essentially of, or consist of) tungsten chloride, molybdenum chloride, or a mixture thereof, alternatively, tungsten chloride; or alternatively, molybdenum chloride.

Optionally, the metal halide based metathesis catalyst system can further comprise a metal alkyl activator (as described herein), oxygen, an alcohol, or any combination thereof; alternatively, a metal alkyl activator; alternatively, oxygen; or alternatively, an alcohol. Non-limiting examples of metal halide based metathesis catalyst systems can include tungsten chloride/tetrabutyl tin ($WCl_6/SnMe_4$), tungsten chloride/ethylaluminum dichloride ($WCl_6/EtAlCl_2$), tungsten chloride/ethylaluminum dichloride/ethyl alcohol ($WCl_6/EtAlCl_2/EtOH$), molybdenum chloride/triethyl aluminum ($MoCl_5/AlEt_3$), and molybdenum chloride/triethyl aluminum/$O_2$ ($MoCl_5/AlEt_3/O_2$). Other suitable metal halide based metathesis catalyst systems are known to those skilled in the art.

Metal carbene based metathesis catalyst systems can comprise (or consist essentially of, or consist of) tungsten, tantalum, osmium, molybdenum, ruthenium, or any combination thereof. For instance, the metal carbene based metathesis catalyst system can comprise (or consist essentially of, or consist of) tungsten; alternatively, tantalum; alternatively, osmium; alternatively, molybdenum; or alternatively, ruthenium. These metal carbene based metathesis catalyst systems can contain compounds which have a stable metal-carbon double bond or can form a metal-carbon double bond in situ from a metal precursor having a stable metal-carbon single bond.

In an embodiment, a ruthenium carbene based metathesis catalyst system can comprise a compound having the structure $L^1L^2X_2Ru=CHR^1$, wherein $L^1$ and $L^2$ can be an organic ligand, X can be a halide, and $R^1$ can be hydrogen or a hydrocarbyl group. Generally, the compound in the ruthenium carbene based metathesis catalyst system having the structure $L^1L^2X_2Ru=CHR^1$ can be described using any combination of $L^1$, $L^2$, X, or $R^1$ described herein.

Generally, $L^1$ and $L^2$ independently can be $R'_3P$, an imidazolinylidene group, or an imidazolidinylidene group. In some embodiments, $L^1$ and $L^2$ can be $R'_3P$; alternatively, $L^1$ can be $R'_3P$ and $L^2$ can be an imidazolinylidene group or an imidazolidinylidene group; alternatively, $L^1$ can be $R'_3P$ and $L^2$ can be an imidazolinylidene group; alternatively, $L^1$ can be $R'_3P$ and $L^2$ can be an imidazolidinylidene group; alternatively, $L^1$ and $L^2$ can be imidazolinylidene groups; or alternatively, $L^1$ and $L^2$ can be imidazolidinylidene groups. In embodiments of this invention, R' can be a hydrocarbyl group, where each R' of $R'_3P$ can be the same; alternatively, each R' of $R'_3P$ can be different; or alternatively, one R' of $R'_3P$ can be different from the other two R' groups. In some embodiments, each R' of $R'_3P$ independently can be a $C_1$ to $C_{15}$ hydrocarbyl group; or alternatively, a $C_1$ to $C_{10}$ hydrocarbyl group. In other embodiments, each hydrocarbyl R' of $R'_3P$ independently can be an alkyl group or an aromatic group; alternatively, an alkyl group; or alternatively, an aromatic group. In an embodiment, each alkyl R' of $R'_3P$ independently can be a methyl group, ethyl group, n-propyl group, isopropyl group, tert-butyl group, neo-pentyl group, cyclopentyl group, or cyclohexyl group. In some embodiments, one or more R' groups of $R'_3P$ can be a phenyl group, or alternatively, a substituted phenyl group. In an embodiment, the substituents of any substituted phenyl group independently can be a $C_1$-$C_5$ organyl group, or alternatively, a $C_1$-$C_5$ hydrocarbyl group. In some embodiments, $R'_3P$ can be a trialkyl phosphine or triphenyl phosphine; alternatively, a trialkyl phosphine; or alternatively, triphenyl phosphine. In an embodiment, $R'_3P$ can be trimethyl phosphine, triethyl phosphine, triisopropyl phosphine, tri-tert-butyl phosphine, tri-neopentyl phosphine, tricyclopentyl phosphine, tricyclohexyl phosphine, or triphenyl phosphine; alternatively, triisopropyl phosphine, tri-tert-butyl phosphine, tri-neopentyl phosphine, tricyclopentyl phosphine, tricyclohexyl phosphine, or triphenyl phosphine; alternatively, tricyclopentyl phosphine, tricyclohexyl phosphine, or triphenyl phosphine; alternatively, tricyclopentyl phosphine or tricyclohexyl phosphine; alternatively, tricyclopentyl phosphine; alternatively, tricyclohexyl phosphine; or alternatively triphenyl phosphine.

In an embodiment, the imidazolinylidene group or imidazolidinylidene group can be a $C_3$ to $C_{80}$ imidazolinylidene group or imidazolidinylidene group; alternatively, a $C_3$ to $C_{50}$ imidazolinylidene group or imidazolidinylidene group; or alternatively, a $C_5$ to $C_{40}$ imidazolinylidene group or imidazolidinylidene group. In some embodiments, the imidazolinylidene group can be a 1,3-disubstituted imidazolinylidene group. In some embodiments, the imidazolidinylidene group can be a 1,3-disubstituted imidazolidinylidene group. In an embodiment, the 1,3-substituents of the 1,3-disubstituted imidazolinylidene group or 1,3-disubstituted imidazolidinylidene group independently can be any suitable hydrocarbyl group. In an embodiment, the 1,3-substituents of the 1,3-disubstituted imidazolinylidene group or 1,3-disubstituted imidazolidinylidene group independently can be a $C_1$ to $C_{30}$ hydrocarbyl group. In some embodiments, the 1,3-substituents of the 1,3-disubstituted imidazolinylidene group or 1,3-disubstituted imidazolidinylidene group independently can be a $C_6$ to $C_{20}$ aromatic group or a $C_1$ to $C_{10}$ alkyl group. In other embodiments, the 1,3-substituents of the 1,3-disubstituted imidazolinylidene group or 1,3-disubstituted imidazolidinylidene group independently can be a $C_6$ to $C_{20}$ aromatic group, or alternatively, a $C_1$ to $C_{10}$ alkyl group. In an embodiment, each aromatic group of the 1,3-disubstituted imidazolinylidene group or 1,3-disubstituted imidazolidinylidene group independently can be a substituted aromatic group. In some embodiments, the substituted aromatic group of the 1,3-disubstituted imidazolinylidene group or 1,3-disubstituted imidazolidinylidene group can be a 2-disubstituted phenyl group, a 2,6-disubstituted phenyl group, or a 2,4,6-trisubstituted phenyl group; alternatively, a 2,6-disubstituted phenyl group; or alternatively, a 2,4,6-trisubstituted phenyl group. Suitable substituents for any substituted phenyl group within the 1,3-disubstituted imidazolinylidene group or 1,3-disubstituted imidazolidinylidene group can include any $C_1$ to $C_{10}$ hydrocarbyl group, or alternatively, any $C_1$ to $C_5$ hydrocarbyl group. In some embodiments, each hydrocarbyl substituent independently can be a methyl group, ethyl group, n-propyl group, iso-propyl group, n-butyl group, sec-butyl group, or tert-butyl group; alternatively, a methyl group, ethyl group, n-butyl group, sec-butyl group, or tert-butyl group; alternatively, a methyl group; alternatively, an ethyl group, alternatively, an isopropyl group; or alternatively, a tert-butyl group. In some embodiments, each substituted aromatic group of the 1,3-disubstituted imidazolinylidene group or 1,3-disubstituted imidazolidinylidene group independently can be a 2,6-diisopropylphenyl group or a 2,4,6-trimethylphenyl group; alternatively, a 2,6-diisopropylphenyl group; or alternatively, a 2,4,6-trimethylphenyl group.

In various embodiments, each X of the compound having the structure $L^1L^2X_2Ru=CHR^1$ independently can be chloride, bromide, or iodide. In an embodiment, X can be chloride. In another embodiment, X can be bromide. In yet another embodiment, X can be iodide. $R^1$ of the compound having the structure $L^1L^2X_2Ru=CHR^1$ can be hydrogen or a $C_1$ to $C_{20}$ hydrocarbyl group. In some embodiments, $R^1$ can be a methyl group, an ethyl group, an isopropyl group, a tert-butyl group, a phenyl group, a 2-methyl-2-propene group, or a 2,2-diphenylethene group. In other embodiments, $R^1$ can be a tert-butyl group, a phenyl group, a 2-methyl-2-propene group, or a 2,2-diphenylethene group; alternatively, hydrogen; alternatively, a tert-butyl group; alternatively, a phenyl group; alternatively, a tert-butyl group; alternatively, a phenyl group; alternatively, a 2-methyl-2-propene group; or alternatively, a 2,2-diphenylethene group.

In some non-limiting embodiments, the ruthenium carbene based metathesis catalyst system can comprise dichloro(phenylmethylene) bis(tricyclohexyl phosphine) ruthenium, dichloro(3-methyl-2-butenylidene) bis(tricyclohexyl phosphine) ruthenium, dichloro(3-methyl-2-butenylidene) bis(tricyclopentyl phosphine) ruthenium, 1,3-bis-(2,4,6-trimethylphenyl)-2-(imidazolidinylidene)(phenyl-methylene)dichloro(tricyclohexyl phosphine) ruthenium, or 1,3-bis-(2,6-diisopropylphenyl)-2-(imidazolidinylidene)(phenylmethylene)dichloro(tricyclohexyl phosphine) ruthenium. In some embodiments, the ruthenium carbene based metathesis catalyst system can comprise dichloro(phenyl-methylene) bis(tricyclohexyl phosphine) ruthenium; alternatively, dichloro(3-methyl-2-butenylidene) bis(tricyclohexyl phosphine) ruthenium; alternatively, 1,3-bis-(2,4,6-trimethylphenyl)-2-(imidazolidinylidene)(phenylmethylene)dichloro(tricyclohexyl phosphine) ruthenium; or alternatively, 1,3-bis-(2,6-diisopropylphenyl)-2-(imidazolidinylidene)(phenylmethylene)dichloro(tricyclohexyl phosphine) ruthenium.

In an embodiment, a molybdenum carbene based metathesis catalyst system can comprise a compound having the structure $Mo(=CHR^2)(NAr)(OR^3)_2$, wherein $R^2$ is a hydrogen or hydrocarbyl group, Ar is a substituted aromatic ring, and $R^3$ is a hydrocarbyl group or a halogenated hydrocarbyl group. Generally, the compound in the molybdenum carbene based metathesis catalyst system having the structure $Mo(=CHR^2)(NAr)(OR^3)_2$ can be described using any combination of $R^2$, Ar, and $R^3$ described herein.

In some embodiments, $R^2$ of the compound having the structure $Mo(=CHR^2)(NAr)(OR^3)_2$ can be hydrogen or a $C_1$ to $C_{20}$ hydrocarbyl group, or alternatively, a $C_1$ to $C_{20}$ hydrocarbyl group. In some embodiments, $R^2$ can be a methyl group, an ethyl group, an isopropyl group, a tert-butyl group, a phenyl group, a 2-methyl-2-propene group, or a 2,2-diphenylethene group. In other embodiments, $R^2$ can be a tert-butyl group, a phenyl group, a 2-methyl-2-propene group, or a 2,2-diphenylethene group; alternatively, a tert-butyl group or a phenyl group; alternatively, hydrogen; alternatively, a tert-butyl group; alternatively, a phenyl group; alternatively, a 2-methyl-2-propene group; or alternatively, a 2,2-diphenylethene group.

In an embodiment, the substituted aromatic ring, Ar, of the compound having the structure $Mo(=CHR^2)(NAr)(OR^3)_2$ can be a $C_6$ to $C_{30}$ aromatic group, or alternatively, a $C_6$ to $C_{20}$ aromatic group. In some embodiments, each substituent of the substituted aromatic ring, Ar, independently can be a $C_6$ to $C_{20}$ hydrocarbyl group, a $C_1$ to $C_{10}$ hydrocarbyl group, or a $C_1$ to $C_5$ hydrocarbyl group. In some embodiments, the substituted aromatic ring, Ar, can be a 2-substituted phenyl group, a 2,6-disubstituted phenyl group, or a 2,4,6-trisubstituted phenyl group. In an embodiment, each substituent of the substituted aromatic ring independently can be a methyl group, an ethyl group, an isopropyl group, a tert-butyl group, or a neopentyl group; alternatively, a methyl group, an isopropyl group, or a tert-butyl group; alternatively, a methyl group or an isopropyl group. In some embodiments, each substituent of the substituted aromatic ring independently can be a methyl group; alternatively, an isopropyl group; or alternatively, a tert-butyl group. In some non-limiting embodiments, the substituted aromatic ring, Ar, can be a 2-tert-butylphenyl group, a 2,6-dimethylphenyl group, a 2,6-diisopropylphenyl group, or a 2,4,6-trimethyl phenyl group; alternatively, a 2-tert-butylphenyl group; alternatively, a 2,6-dimethylphenyl group; alternatively, a 2,6-diisopropylphenyl group; or alternatively, a 2,4,6-trimethyl phenyl group.

In an embodiment, each $R^3$ of the compound having the structure $Mo(=CHR^2)(NAr)(OR^3)_2$ independently can be a $C_1$ to $C_{10}$ organic group, or alternatively, a $C_1$ to $C_5$ organic group. In some embodiments, the $C_1$ to $C_{10}$ or $C_1$ to $C_5$ organic group can be a hydrocarbylhalyl group (a group consisting of hydrogen, carbon, and halogen atoms); alternatively, a hydrocarbylfluoryl group (a group consisting of hydrogen, carbon, and fluorine atoms); or alternatively, a hydrocarbyl group. In an embodiment, the halogen atoms of the hydrocarbylhalyl group can be fluorine, chlorine, bromine, iodine, or any combination thereof; alternatively, fluorine; alternatively, chlorine; alternatively, bromine; or alternatively, iodine. In some embodiments, each $R^3$ independently can be a tert-butyl group or a hexafluoro-tert-butyl group. In other embodiments, $(OR^3)_2$ can represent a single organic group wherein the two $R^3$ groups attached to the oxygen atoms are connected via a bond between any divalent, trivalent, or tetravalent atom within the $R^3$ groups. In further embodiments, $(OR^3)_2$ can represent a single organic group wherein the two $R^3$ groups attached to the oxygen atoms are connected via a carbon-carbon bond between any carbon atom of the two $R^3$ groups.

In an embodiment, the molybdenum carbene based metathesis catalyst system can comprise $Mo(=CH-C(CH_3)_3)(N-2,6-diisopropylphenyl)(OC(CH_3)_3)$, $Mo(=CH-C(CH_3)_2(C_6H_5))(N-2,6-diiso-propylphenyl)(OC(CH_3)_3)$, $Mo(=CH-C(CH_3)_3)(N-2,6-diisopropylphenyl)(OC(CH_3)(CF_3)_2)$, or $Mo(=CH-C(CH_3)_2(C_6H_5))(N-2,6-diisopropylphenyl)(OC(CH_3)(CF_3)_2)$. In other embodiments, the molybdenum carbene based metathesis catalyst system can comprise $Mo(=CH-C(CH_3)_3)(N-2,6- diiso-propylphenyl)(OC(CH$_3$)$_3$); alternatively, Mo(=CH—C(CH$_3$)$_2$(C$_6$H$_5$))(N-2,6-diisopropylphenyl)(OC(CH$_3$)$_3$); alternatively, Mo(=CH—C(CH$_3$)$_3$)(N-2,6-diisopropylphenyl)(OC(CH$_3$)(CF$_3$)$_2$); or alternatively, Mo(=CH—C(CH$_3$)$_2$(C$_6$H$_5$))(N-2,6-diisopropylphenyl)(OC(CH$_3$)(CF$_3$)$_2$).

Optionally, the metal carbene based metathesis catalyst system can further comprise a support. Illustrative supports can include alumina, silica, silica-alumina, and aluminum-phosphate, amongst other solid oxide materials. Additionally, the support can comprise a polymer, and the metal carbene metathesis catalyst compound can be tethered to the support via any of the ligands which do not contain the metal-carbon double bond.

Any suitable conditions for the metathesis step can be employed, as would be recognized by those skilled in the art in view of this disclosure and the examples that follow, and U.S. Pat. No. 8,765,984.

Referring now to step (ii) of the processes disclosed herein, which often is referred to as the hydroformylation step. In this step, a linear internal olefin—such as that formed in the metathesis step—can be contacted with a hydroformylation catalyst system, carbon monoxide, and hydrogen to form a linear aldehyde having the formula CH$_3$(CH$_2$)$_{2n+3}$C(=O)H. As described herein, n can be an integer ranging from 0 to 15; for example, n can be an integer from 0 to 10, n can be an integer from 0 to 7, n can be an integer from 1 to 7, or n can be an integer from 1 to 5.

Consistent with certain embodiments of this invention, step (ii) can comprise contacting the linear internal olefin with a hydroformylation catalyst system and syngas (also referred to as synthesis gas) to form the linear aldehyde. As would be recognized by those skilled in the art, syngas is a mixture containing predominately carbon monoxide and hydrogen. Syngas also can contain carbon dioxide and methane in lesser amounts.

Any suitable hydroformylation catalyst system can be used in the hydroformylation step, non-limiting examples of which can include a rhodium compound, a cobalt compound, a ruthenium compound, an iridium compound, a platinum compound, a palladium compound, an iron compound, or any combination thereof. For instance, the hydroformylation catalyst system can comprise a rhodium compound; alternatively, a cobalt compound; alternatively, a ruthenium compound; alternatively, an iridium compound; alternatively, a platinum compound; alternatively, a palladium compound; or alternatively, an iron compound.

Any suitable conditions for the hydroformylation step can be employed, as would be recognized by those skilled in the art in view of this disclosure, and in particular, the examples that follow.

Referring now to step (iii) of the processes disclosed herein, which often is referred to as the dehydroformylation step. In this step, a linear aldehyde—such as that formed in the hydroformylation step—can be contacted with a dehydroformylation catalyst system comprising i) a transition metal compound, a diphosphine, and a carboxylic acid or carboxylic acid derivative, or ii) a diphosphine transition metal compound complex and a carboxylic acid or carboxylic acid derivative, to form a second normal alpha olefin having the structure CH$_3$(CH$_2$)$_{2n+1}$HC=CH$_2$. As described herein, n can be an integer ranging from 0 to 15; for example, n can be an integer from 0 to 10, n can be an integer from 0 to 7, n can be an integer from 1 to 7, or n can be an integer from 1 to 5. Accordingly, in some embodiments, the second normal alpha olefin can comprise (or consist essentially of, or consist of) 1-butene, 1-hexene, 1-octene, 1-decene, 1-dodecene, 1-tetradecene, 1-hexadecene, 1-octadecene, or as any combination thereof; alternatively, 1-hexene, 1-octene, 1-decene, 1-dodecene, 1-tetradecene, or any combination thereof; or alternatively, 1-hexene, 1-octene, 1-decene, or any combination thereof. In other embodiments, the second normal alpha olefin can comprise (or consist essentially of, or consist of) 1-hexene; alternatively, 1-octene; or alternatively, 1-decene.

In an embodiment of this invention, the dehydroformylation step can be conducted in the substantial absence of an aldehyde group acceptor (e.g., an acceptor olefin, among others)—i.e., the step can be conducted "acceptorless." Generally, in the substantial absence of an aldehyde group acceptor (e.g., acceptor olefin, among others) means that the dehydroformylation step is performed with less than 1, 0.5, 0.25, 0.1, 0.05, 0.025, 0.01 mole % of an aldehyde group acceptor (e.g., acceptor olefin, among others) based upon the amount of aldehyde in the dehydroformylation step. However, in another embodiment, the dehydroformylation step can be conducted in the presence of an aldehyde group acceptor (e.g., acceptor olefin, among others). In these embodiments, step (iii) can comprise contacting the linear aldehyde with 1) a dehydroformylation catalyst system comprising i) a transition metal compound, a diphosphine, and a carboxylic acid or carboxylic acid derivative, or ii) a diphosphine transition metal compound complex and a carboxylic acid or carboxylic acid derivative, and 2) an aldehyde group acceptor, to form a second normal alpha olefin having the structure CH$_3$(CH$_2$)$_{2n+1}$HC=CH$_2$.

The aldehyde group acceptor can be any suitable compound having at least one carbon-carbon double bond. Generally, the aldehyde group acceptor can have any combination of the features for the aldehyde group acceptor having at least one carbon-carbon double bond described herein. In an embodiment, the aldehyde group acceptor used in the dehydroformylation step can have at least 2 carbon atoms, at least 3 carbon atoms, at least 4 carbon atoms, or at least 5 carbon atoms. In some embodiments, the aldehyde group acceptor used in the dehydroformylation step can have a maximum of 100 carbon atoms, 80 carbon atoms, 60 carbon atoms, 50 carbon atoms, 40 carbon atoms, 30 carbon atoms, 25 carbon atoms, 20 carbon atoms, 15 carbon atoms, or 10 carbon atoms. Generally, the aldehyde group acceptor used in the dehydroformylation step can have from any minimum number of carbon atoms described herein to any maximum number of carbon atoms described herein. For example, in some non-limiting embodiments, the aldehyde group acceptor can have from 2 to 100 carbon atoms, from 3 to 80 carbon atoms, from 4 to 60 carbon atoms, or from 5 to 60 carbon atoms. Other carbon atom number ranges can be readily envisioned from the present disclosure and are encompassed herein.

In an embodiment, the aldehyde group acceptor can be a hydrocarbon compound, a heteroatomic compound, or any combination thereof; alternatively, a hydrocarbon compound; or alternatively, a heteroatomic compound. In some embodiments, the aldehyde group acceptor can be aliphatic, aromatic, or any combination thereof; alternatively, aliphatic; or alternatively, aromatic. In other embodiments, the aldehyde group acceptor can be acyclic, cyclic, or any combination thereof; alternatively, acyclic; or alternatively, cyclic.

The aldehyde group acceptor used in dehydroformylation step can have at least one carbon-carbon double bond. In one embodiment, the aldehyde group acceptor has from 1 to 10 double bonds; alternatively, from 1 to 8 double bonds;

alternatively, from 3 to 5 double bonds; or alternatively, from 2 to 4 double bonds. In another embodiment, the aldehyde group acceptor can have only one carbon-carbon double bond; alternatively, only two double bonds; alternatively, only three double bonds; alternatively, only four double bonds; alternatively, only five double bonds; or alternatively, only six double bonds. In some embodiments, the aldehyde group acceptor can be an acceptor olefin.

Representative and non-limiting examples of acceptor olefins having only one carbon-carbon double bond can comprise, consist essentially of, or consist of, either singly or in any combination, ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, 1-undecene, 1-dodecene, 1-tridecene, 1-tetradecene, 1-pentadecene, or styrene.

Representative and non-limiting examples of cyclic acceptor olefins acceptor having only one carbon-carbon double bond can comprise, consist essentially of, or consist of, either singly or in any combination, norbornene, cyclopentene, cyclohexene, cycloheptene, or cyclooctene. In some embodiments, cyclic acceptor olefins having only one carbon-carbon double bond can comprise, consist essentially of, or consist of, norbornene; alternatively, cyclopentene; alternatively, cyclohexene; alternatively, cycloheptene; or alternatively, cyclooctene.

Illustrative examples of acceptor olefins having at least two carbon-carbon double bonds that can be employed in the dehydroformylation step can comprise, consist essentially of, or consist of, either singly or in any combination, butadiene, isoprene, cyclobutadiene, cyclopentadiene, cyclohexadiene, cyclooctadiene, norbornadiene, vinylcyclohexene, vinylnorbornene, divinylbenzene, or cyclopentadiene dimer. Hence, mixtures or combinations of more than one acceptor olefin can be employed. Accordingly, the acceptor olefin having at least two double bonds can comprise, consist essentially of, or consist of, either singly or in any combination, butadiene, isoprene, cyclobutadiene, cyclopentadiene, cyclohexadiene, or cyclooctadiene; alternatively, norbornadiene, vinylcyclohexene, vinylnorbornene, or divinylbenzene; alternatively, butadiene; alternatively, isoprene; alternatively, cyclobutadiene; alternatively, cyclopentadiene; alternatively, cyclohexadiene; alternatively, cyclooctadiene; alternatively, norbornadiene; alternatively, vinylcyclohexene; alternatively, vinylnorbornene; alternatively, divinylbenzene; or alternatively, cyclopentadiene dimer.

In an embodiment, the acceptor olefin can comprise, consist essentially of, or consist of, one or more compounds having only three carbon-carbon double bonds. Illustrative non-limiting examples of such compounds can comprise, consist essentially of, or consist of, singly or in any combination, trivinylcyclohexane, trivinylbenzene, cycloheptatriene, dimethyl heptatriene, octatriene, cyclooctatriene, or cyclododecatriene. In one embodiment, the acceptor olefin can comprise, consist essentially of, or consist of, trivinylcyclohexane. In another embodiment, the acceptor olefin can comprise, consist essentially of, or consist of, trivinylbenzene. In another embodiment, the acceptor olefin can comprise, consist essentially of, or consist of, cycloheptatriene. In another embodiment, the acceptor olefin can comprise, consist essentially of, or consist of, dimethyl heptatriene. In another embodiment, the acceptor olefin can comprise, consist essentially of, or consist of, octatriene. Yet, in another embodiment, the acceptor olefin can comprise, consist essentially of, or consist of, cyclooctatriene. In still another embodiment, the acceptor olefin can comprise, consist essentially of, or consist of, cyclododecatriene.

Acceptor olefins having four or more carbon-carbon bonds also are contemplated. For instance, the acceptor olefin can comprise, consist essentially of, or consist of, cyclooctatetraene; alternatively, cyclododecatetraene; alternatively, a polybutadiene; or alternatively, a combination of two or more of these compounds.

In some embodiments, the aldehyde group acceptor can comprise, consist essentially of, or consist of, an unsaturated triglyceride, while in other embodiments, the aldehyde group acceptor can comprise, consist essentially of, or consist of, an unsaturated natural source oil. In an embodiment, the aldehyde group acceptor can comprise, consist essentially of, or consist of, either singly or in any combination, soybean oil, corn oil, castor bean oil, or canola oil. In other embodiments, the aldehyde group acceptor can comprise an unsaturated carboxylic acid, an ester of an unsaturated carboxylic acid (e.g., methyl, ethyl ester, propyl, or butyl ester), or any combination thereof; alternatively, an unsaturated carboxylic acid; or alternatively, an ester of an unsaturated carboxylic acid. In some embodiments, the unsaturated carboxylic acid, or the unsaturated carboxylic acid portion of the unsaturated carboxylic acid ester, which can be utilized as the the aldehyde group acceptor can comprise, consist essentially of, or consist of, vinyl acetic acid, 3-pentenoic acid, maleic acid, fumaric acid, sorbic acid, caproleic acid, lauroleic acid, myristoleic acid, palmitoleic acid, oleic acid, ricinoleic acid, linoleic acid, linolenic acid, or any combination thereof. In yet another embodiment, the aldehyde group acceptor can comprise an unsaturated carboxylic acid anhydride (e.g., maleic anhydride).

When used in the dehydroformylation step, the amount of the aldehyde group acceptor is not particularly limited. For instance, the dehydroformylation step can be conducted and/or the second normal alpha olefin can be formed at a minimum aldehyde group acceptor (e.g., acceptor olefin) to linear aldehyde molar ratio of 0.2:1, 0.5:1, 0.75:1, 1:1, 1.5:1, or 2:1; or additionally or alternatively, at a maximum aldehyde group acceptor (e.g., acceptor olefin) to linear aldehyde molar ratio of 1000:1, 500:1, 100:1, 50:1, 25:1, 10:1, or 5:1. In an embodiment, the aldehyde group acceptor (e.g., acceptor olefin) to linear aldehyde molar ratio can be in a range from any minimum aldehyde group acceptor (e.g., acceptor olefin) to linear aldehyde molar ratio disclosed herein to any maximum aldehyde group acceptor (e.g., acceptor olefin) to linear aldehyde molar ratio disclosed herein. In some non-limiting embodiments, the molar ratio can be in a range from 0.2:1 to 1000:1, from 0.5:1 to 500:1, from 0.75:1 to 100:1, from 1:1 to 10:1, or from 0.5:1 to 5:1. Other molar ratios of the aldehyde group acceptor (e.g., acceptor olefin) to the linear aldehyde are readily apparent from this disclosure. As those skilled in the art would readily recognize, the aldehyde group acceptor (e.g., acceptor olefin) to linear aldehyde molar ratio can change as the dehydroformylation reaction proceeds. Accordingly, these ranges of molar ratios are meant to encompass the initial reactant ratio as well as any molar ratio of the aldehyde group acceptor (e.g., acceptor olefin) to the linear aldehyde encountered as the dehydroformylation reaction proceeds.

Any suitable dehydroformylation catalyst system can be used in the dehydroformylation step, whether the diphosphine transition metal compound complex is formed in-situ or is pre-formed. For example, the dehydroformylation catalyst system can comprise any suitable transition metal compound, any suitable diphosphine, and any suitable carboxylic acid or carboxylic acid derivative. Generally, the transition metal compound, the diphosphine, and the carboxylic acid or carboxylic acid derivative are independent elements of the dehydroformylation catalyst system and are independently described herein. Consequently, the dehydroformylation catalyst system can be described utilizing any combination of the transition metal compound disclosed herein, the diphosphine disclosed herein, and the carboxylic acid or carboxylic acid derivative disclosed herein. In another embodiment, the dehydroformylation catalyst system can comprise any suitable diphosphine transition metal compound complex and any suitable carboxylic acid or carboxylic acid derivative. In this dehydroformylation catalyst system embodiment, the diphosphine transition metal compound complex and the carboxylic acid or carboxylic acid derivative are independent elements of the dehydroformylation catalyst system and are independently described herein. Consequently, the dehydroformylation catalyst system can be described utilizing any combination of the transition metal compound complex disclosed herein and the carboxylic acid or carboxylic acid derivative disclosed herein.

The transition metal of the transition metal compound or the diphosphine transition metal compound complex can be a Group 3 to Group 10 transition metal, a Group 4 to Group 11 transition metal, a Group 4 to Group 9 transition metal, a Group 8 to Group 10 transition metal, or a Group 9 transition metal. For instance, the transition metal of the transition metal compound or the diphosphine transition metal compound complex can be cobalt, rhodium, or iridium; alternatively, cobalt; alternatively, rhodium; or alternatively, iridium. Accordingly, in an embodiment of this invention, the transition metal compound can comprise a rhodium compound, non-limiting examples of which can include an olefin rhodium alkoxide complex, a cyclodiene rhodium alkoxide complex, or any combination thereof; alternatively, an olefin rhodium alkoxide complex; or alternatively, a cyclodiene rhodium alkoxide complex.

The diphosphine or the diphosphine of the diphosphine transition metal compound complex can have the following structure:

(I)

In structure (I), $L^1$ can be any suitable linking group or any linking group disclosed herein, and each R independently can be H or any $C_1$ to $C_{18}$ hydrocarbyl group disclosed herein. For instance, each R independently can be H or a $C_1$ to $C_{12}$ hydrocarbyl group, or H or a $C_1$ to $C_6$ hydrocarbyl group; alternatively, H or a $C_1$ to $C_{18}$ alkyl group, $C_2$ to $C_{18}$ alkenyl group, $C_6$ to $C_{18}$ aryl group, or $C_7$ to $C_{18}$ aralkyl group; or alternatively, H or a $C_1$ to $C_5$ alkyl group, $C_2$ to $C_5$ alkenyl group, $C_6$ to $C_8$ aryl group, or $C_7$ to $C_8$ aralkyl group. Each R independently in structure (I) can be, in certain embodiments, H, a methyl group, an ethyl group, a propyl group, a butyl group, a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group, a benzyl group, or a naphthyl group. In other embodiments, each R independently can be H, a methyl group, an ethyl group, a propyl group, a butyl group, a pentyl group, a hexyl group, a heptyl group, an octyl group, a nonyl group, or a decyl group; alternatively, H, an ethenyl group, a propenyl group, a butenyl group, a pentenyl group, a hexenyl group, a heptenyl group, an octenyl group, a nonenyl group, or a decenyl group; or alternatively, H, a phenyl group, a tolyl group, a benzyl group, or a naphthyl group.

In one embodiment, the diphosphine or the diphosphine of the diphosphine transition metal compound complex can comprise (or consist essentially of, or consist of) a 1,6-bis(dihydrocarbylphosphinyl)hexane, a substituted 1,6-bis(dihydrocarbylphosphinyl)hexane, a (1,3-phenylenedi-1,1-ethanediyl)bis(dihydrocarbylphosphine), a substituted (1,3-phenylenedi-1,1-ethanediyl)-bis(dihydrocarbylphosphine), a 1,8-anthracenediylbis(dihydrocarbylphosphine), a substituted 1,8-anthracenediylbis(dihydrocarbylphosphine), a 1,8-tetradecahydroanthracenediylbis(dihydrocarbylphosphine), a substituted 1,8-tetradecahydroanthracenediylbis(dihydrocarbylphosphine), a (methylenedi-2,1-phenylene)bis(dihydrocarbylphosphine), a substituted (methylenedi-2,1-phenylene)bis(dihydrocarbylphosphine), a 9H-xanthene-4,5-diylbis(dihydrocarbylphosphine), or a substituted 9H-xanthene-4,5-diylbis(dihydrocarbylphosphine). For example, the diphosphine or the diphosphine of the diphosphine transition metal compound complex can comprise (or consist essentially of, or consist of) a 1,6-bis(dihydrocarbylphosphinyl)hexane; alternatively, a substituted 1,6-bis(dihydrocarbylphosphinyl)hexane; alternatively, a (1,3-phenylenedi-1,1-ethanediyl)-bis(dihydrocarbylphosphine); alternatively, a substituted (1,3-phenylenedi-1,1-ethanediyl) bis-(dihydrocarbylphosphine); alternatively, a 1,8-anthracenediylbis(dihydrocarbylphosphine); alternatively, a substituted 1,8-anthracenediylbis(dihydrocarbylphosphine); alternatively, a 1,8-tetradecahydroanthracenediylbis(dihydrocarbylphosphine); alternatively, a substituted 1,8-tetradecahydroanthracenediylbis(dihydrocarbylphosphine); alternatively, a (methylene di-2,1-phenylene)bis(dihydrocarbylphosphine); alternatively, a substituted (methylene di-2,1-phenylene)bis(dihydrocarbylphosphine); alternatively, a 9H-xanthene-4,5-diylbis(dihydrocarbylphosphine); or alternatively, a substituted 9H-xanthene-4,5-diylbis(dihydrocarbylphosphine). Each hydrocarbyl independently can be any suitable hydrocarbyl group or any $C_1$ to $C_{18}$ hydrocarbyl group, $C_1$ to $C_{12}$ hydrocarbyl group, or $C_1$ to $C_6$ hydrocarbyl group disclosed herein.

In another embodiment, the diphosphine or the diphosphine of the diphosphine transition metal compound complex can comprise (or consist essentially of, or consist of) a 1,6-bisphosphinylhexane, a substituted 1,6-bisphosphinylhexane, a (1,3-phenylenedi-1,1-ethanediyl)bis(phosphine), a substituted (1,3-phenylenedi-1,1-ethanediyl)bis(phosphine), a 1,8-anthracenediylbis(phosphine), a substituted 1,8-anthracenediylbis(phosphine), a 1,8-tetradecahydro-anthracenediylbis(phosphine), a substituted 1,8-tetradecahydroanthracenediylbis(phosphine), a (methylenedi-2,1-phenylene) bis(phosphine), a substituted (methylenedi-2,1-phenylene) bis-(phosphine), a 9H-xanthene-4,5-diylbis(phosphine), or a substituted 9H-xanthene-4,5-diylbis(phosphine). For example, the diphosphine or the diphosphine of the diphosphine transition metal compound complex can comprise (or consist essentially of, or consist of) a 1,6-bisphosphinylhexane; alternatively, a substituted 1,6-bisphosphinylhexane; alternatively, a (1,3-phenylenedi-1,1-ethanediyl)bis (phosphine); alternatively, a substituted (1,3-phenylenedi-1,1-ethanediyl)bis(phosphine); alternatively, a 1,8-anthracenediylbis(phosphine); alternatively, a substituted 1,8-anthracenediylbis(phosphine); alternatively, a 1,8-tetradecahydroanthracenediylbis(phosphine); alternatively, a substituted 1,8-tetradecahydroanthracenediylbis(phosphine); alternatively, a (methylenedi-2,1-phenylene)bis(phosphine); alternatively, a substituted (methylenedi-2,1-phenylene)bis(phosphine); alternatively, a 9H-xanthene-4,5-diylbis(phosphine); or alternatively, a substituted 9H-xanthene-4,5-diylbis(phosphine).

In yet another embodiment, the diphosphine or the diphosphine of the diphosphine transition metal compound complex can comprise (or consist essentially of, or consist of) a (9,9-dimethyl-9H-xanthen-4,5-diyl)bis(phosphine) or a substituted (9,9-dimethyl-9H-xanthen-4,5-diyl)bis(phosphine); alternatively, a (9,9-dimethyl-9H-xanthen-4,5-diyl)bis(phosphine); or alternatively, a substituted (9,9-dimethyl-9H-xanthen-4,5-diyl)bis(phosphine).

In still another embodiment, the diphosphine or the diphosphine of the transition metal compound complex can have any one of the following structures, wherein Ph is a phenyl group, and each R independently can be H or any $C_1$ to $C_{18}$ hydrocarbyl group disclosed herein (e.g., H or a $C_1$ to $C_{12}$ hydrocarbyl group; alternatively, H or a $C_1$ to $C_6$ hydrocarbyl group; alternatively, H or a $C_1$ to $C_{18}$ alkyl group, $C_2$ to $C_{18}$ alkenyl group, $C_6$ to $C_{18}$ aryl group, or $C_7$ to $C_{18}$ aralkyl group; or alternatively, H or a $C_1$ to $C_5$ alkyl group, $C_2$ to $C_5$ alkenyl group, $C_6$ to $C_8$ aryl group, or $C_7$ to $C_8$ aralkyl group):

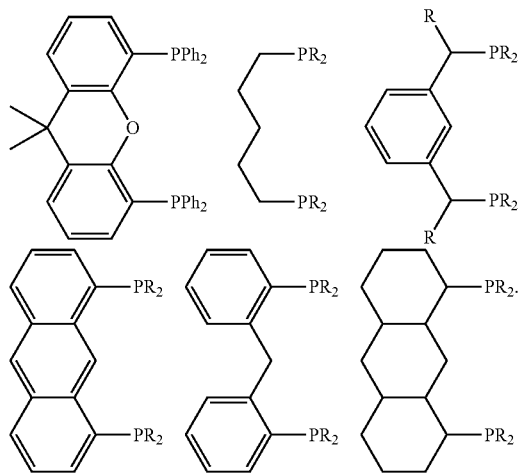

The amount of the transition metal in the dehydroformylation catalyst system relative to the amount of the linear aldehyde is not particularly limited. For instance, the minimum molar ratio of the linear aldehyde to the transition metal (of the transition metal compound or the diphosphine transition metal compound complex) can be 0.00001:1, 0.0001:1, 0.0005:1, or 0.001:1; additionally or alternatively, the maximum molar ratio of the linear aldehyde to the transition metal can be 0.05:1, 0.03:1, 0.02:1, or 0.01:1. In an embodiment, the linear aldehyde to transition metal (of the transition metal compound or the diphosphine transition metal compound complex) molar ratio can be in a range from any minimum linear aldehyde to transition metal molar ratio disclosed herein to any maximum linear aldehyde to transition metal molar ratio disclosed herein. In some non-limiting embodiments, the molar ratio can be in a range from 0.00001:1 to 0.05:1, from 0.0001:1 to 0.03:1, from 0.0005:1 to 0.02:1, or from 0.001:1 to 0.01:1. Other molar ratios of the linear aldehyde to transition metal are readily apparent from this disclosure. As those skilled in the art would readily recognize, the linear aldehyde to transition metal molar ratio can change as the dehydroformylation reaction proceeds. Accordingly, these ranges of molar ratios are meant to encompass the initial ratio as well as any molar ratio of the linear aldehyde to transition metal encountered as the dehydroformylation reaction proceeds.

In circumstances where the dehydroformylation catalyst system comprises a transition metal compound, a diphosphine, and a carboxylic acid or carboxylic acid derivative, the minimum molar ratio of the transition metal (of the transition metal compound) to the diphosphine can be 0.8:1, 0.85:1, 0.9:1, or 0.95:1; additionally or alternatively, the maximum molar ratio of the transition metal to the disphosphine can be 5:1, 4:1, 3:1, or 2.5:1. In an embodiment, the transition metal (of the transition metal compound) to diphosphine molar ratio can be in a range from any minimum transition metal to diphosphine molar ratio disclosed herein to any maximum transition metal to diphosphine molar ratio disclosed herein. In some non-limiting embodiments, the molar ratio can be in a range from 0.8:1 to 5:1, from 0.85:1 to 4:1, from 0.9:1 to 3:1, or from 0.95:1 to 2.5:1. Other molar ratios of the transition metal to the diphosphine are readily apparent from this disclosure.

The specific carboxylic acid or carboxylic acid derivative used in the dehydroformylation step is not particularly limited. In some embodiments, the carboxylic acid or carboxylic acid derivative can be an aliphatic carboxylic acid or carboxylic acid derivative, while in other embodiments, the carboxylic acid or carboxylic acid derivative can be an aromatic carboxylic acid or carboxylic acid derivative. The carboxylic acid can be any suitable $C_1$ to $C_{24}$ carboxylic acid or any $C_1$ to $C_{24}$ carboxylic acid disclosed herein, either substituted or unsubstituted. Non-limiting examples of carboxylic acids that can be used in the dehydroformylation step can include formic acid, acetic acid, propionic acid, butanoic acid, pentanoic acid, hexanoic acid, stearic acid, acrylic acid, methacrylic acid, cinnamic acid, benzoic acid, salicylic acid, adipic acid, citric acid, or any combination thereof.

As used herein, "carboxylic acid derivative" is meant to encompass salts and esters of carboxylic acids. In an embodiment, the carboxylic acid derivative can be a carboxylic acid salt, a carboxylic acid ester, or any combination thereof; alternatively, a carboxylic acid salt; or alternatively, a carboxylic acid ester. Typical carboxylic acid salts can include alkali metal or alkaline earth metal salts (e.g., sodium, calcium, magnesium) of the carboxylic acid, while esters refers to compounds where at least one —OH group of the carboxylic acid is replaced by an alkoxy group (e.g., formates, acetates, hexanoates, stearates, acrylates, cinnamates, benzoates, and the like). Similar to the carboxylic acid, the carboxylic acid derivative can be any suitable $C_1$ to $C_{24}$ carboxylic acid derivative or any $C_1$ to $C_{24}$ carboxylic acid derivative disclosed herein, either substituted or unsubstituted. In an embodiment, each substituent can be a $C_1$ to $C_8$ hydrocarbyl group, a $C_1$ to $C_5$ hydrocarbyl group, a $C_1$ to $C_8$ alkyl group, or a $C_1$ to $C_5$ alkyl group. In an embodiment, the carboxylic acid ester can be a methyl ester, an ethyl ester, a propyl ester, or a butyl ester of any carboxylic acid described herein. As a representative example, the carboxylic acid or carboxylic acid derivative can comprise benzoic acid (or a substituted benzoic acid) or a salt or ester of benzoic acid (or a salt or ester of a substituted benzoic acid).

The amount of the carboxylic acid or carboxylic acid derivative used in the dehydroformylation step is not particularly limited, but generally, the minimum molar ratio of the transition metal (of the transition metal compound or the diphosphine transition metal compound complex) to the carboxylic acid or carboxylic acid derivative can be 0.8:1, 0.85:1, 0.9:1, or 0.95:1; additionally or alternatively, the maximum molar ratio of the transition metal to the carboxylic acid or carboxylic acid derivative can be 5:1, 3:1, 2:1, or 1.5:1. In an embodiment, the transition metal (of the transition metal compound or the diphosphine transition metal compound complex) to carboxylic acid or carboxylic acid derivative molar ratio can be in a range from any minimum transition metal to carboxylic acid or carboxylic acid derivative molar ratio disclosed herein to any maximum transition metal to carboxylic acid or carboxylic acid derivative molar ratio disclosed herein. In some non-limiting embodiments, the molar ratio can be in a range from in a range from 0.8:1 to 5:1, from 0.85:1 to 3:1, from 0.9:1 to 2:1, or from 0.95:1 to 1.5:1. Other molar ratios of the transition metal (of the transition metal compound or the diphosphine transition metal compound complex) to the carboxylic acid or carboxylic acid derivative are readily apparent from this disclosure.

The dehydroformylation step of the process for forming the second normal alpha olefin can be conducted at a variety of temperatures, pressures, and time periods. For instance, the temperature at which the linear aldehyde and the dehydroformylation catalyst system (and optional aldehyde group acceptor) are initially combined can be the same as, or different from, the temperature at which the second normal alpha olefin is formed. As an illustrative example, the linear aldehyde and the dehydroformylation catalyst system (and optional aldehyde group acceptor) can be initially charged or combined at temperature T1 and, after this initial charging of these materials, the temperature can be changed to a temperature T2 to allow for the dehydroformylation reaction to proceed to form the second normal alpha olefin. Likewise, the pressure can be varied throughout the process.

In an embodiment, the dehydroformylation step can be conducted and/or the second normal alpha olefin can be formed at any suitable temperature. For instance, the dehydroformylation step can be conducted and/or the second normal alpha olefin can be formed at a minimum temperature of 0° C., 10° C., 15° C., or 20° C.; additionally or alternatively, at a maximum temperature of 150° C., 125° C., 100° C., or 75° C. In an embodiment, the dehydroformylation step can be conducted and/or the second normal alpha olefin can be formed in a range from any minimum temperature disclosed herein to any maximum temperature disclosed herein. In some non-limiting embodiments, the temperature can be in a range from 0° C. to 150° C.; alternatively, from 0° C. to 100° C.; alternatively, from 10° C. to 125° C.; alternatively, from 10° C. to 75° C.; alternatively, from 15° C. to 150° C.; alternatively, from 15° C. to 100° C.; alternatively, from 20° C. to 125° C.; or alternatively, from 20° C. to 75° C. Other temperature ranges are readily apparent from this disclosure. These temperature ranges also are meant to encompass circumstances where the dehydroformylation step is conducted and/or the second normal alpha olefin is formed at a series of different temperatures, instead of at a single fixed temperature, falling within the respective temperature ranges.

Generally, the dehydroformylation step can be conducted and/or the second normal alpha olefin can be formed at any suitable pressure, and this can vary depending upon the particular aldehyde group acceptor that is used (e.g., to maintain the aldehyde group acceptor in the liquid phase). For instance, the dehydroformylation step can be conducted and/or the second normal alpha olefin can be formed at a minimum pressure of 0 psig (0 kPa), 5 psig (34 kPa), or 10 psig (69 kPa); additionally or alternatively, at a maximum pressure of 2000 psig (13,785 kPa), 1000 psig (6,890 kPa), 750 psig (5,170 kPa), 500 psig (3,450 kPa), 250 psig (1,720 kPa), 150 psig (1,030 kPa), or 100 psig (689 kPa). In an embodiment, the pressure can be in a range from any minimum pressure disclosed herein to any maximum pressure disclosed herein. While not being limited thereto, the dehydroformylation step can be conducted and/or the second normal alpha olefin can be formed at a reaction pressure in a range from 0 to 2000 psig (0 to 13,785 kPa), from 10 to 2000 psig (69 to 13,785 kPa), from 0 to 1000 psig (0 to 6,890 kPa), from 5 to 1000 psig (34 to 6,890 kPa), from 5 to 750 psig (34 to 5,170 kPa), from 5 to 500 psig (34 to 3,450 kPa), from 5 to 250 psig (34 to 1,720 kPa), from 5 to 150 psig (34 to 1,030 kPa), or from 10 to 100 psig (69 to 689 kPa). In some embodiments, the dehydroformylation step can be conducted and/or the second normal alpha olefin can be formed at atmospheric pressure, while in other embodiments, the dehydroformylation step can be conducted and/or the second normal alpha olefin can be formed at sub-atmospheric pressures. These pressure ranges also are meant to encompass circumstances where the dehydroformylation step is conducted and/or the second normal alpha olefin is formed at a series of different pressures, instead of at a single fixed pressure, falling within the respective pressure ranges.

The dehydroformylation step can be conducted in any suitable reactor or vessel in order to form the second normal alpha olefin, non-limiting examples of which can include a fixed bed reactor, a stirred tank reactor, a plug flow reactor, and a tubular reactor, including more than one reactor in series or in parallel, and including any combination of reactor types and arrangements. The dehydroformylation step disclosed herein can be a batch process in some embodiments, while in other embodiments, the dehydroformylation step can be a continuous process.

Consistent with an embodiment of this invention, the dehydroformylation step can be a continuous process and/or a flow process. For instance, the linear aldehyde and the aldehyde group acceptor (if used) can contact a fixed bed of the dehydroformylation catalyst system at any suitable weight hourly space velocity (WHSV) and at any suitable targeted single pass conversion. Moreover, in a flow or continuous process, multi-passes can be used to increase the overall conversion of the linear aldehyde to the second normal alpha olefin.

In an embodiment, the dehydroformylation step can be conducted and/or the second normal alpha olefin can be formed in a minimum reaction time of 5 minutes, 15 minutes, 45 minutes, or 1 hour; additionally or alternatively, in a maximum reaction time of 100 hours, 75 hours, 50 hours, 24 hours, 10 hours, or 5 hours. Generally, the dehydroformylation step can be conducted and/or the second normal alpha olefin can be formed in a time period ranging from any minimum reaction time disclosed herein to any maximum reaction time disclosed herein. In some non-limiting embodiments, the reaction time can be in a range from 5 minutes to 100 hours; alternatively, from 15 minutes to 75 hours; alternatively, from 15 minutes to 50 hours; alternatively, from 45 minutes to 75 hours; alternatively, from 45 minutes to 24 hours; alternatively, from 1 hour to 24 hours; alternatively, from 1 hour to 10 hours; or alternatively, from 1 hour to 5 hours. Other reaction times are readily apparent from this disclosure. Depending upon the process and/or type of reactor used, the minimum reaction time, maximum reaction time, and reaction time range can be the average minimum reaction time, average maximum reaction time, and average reaction time range.

In particular embodiments of this invention, the linear aldehyde and the dehydroformylation catalyst system can be contacted in the absence of a solvent. However, in other embodiments, the linear aldehyde and the dehydroformylation catalyst system can be contacted in the presence of a solvent. Typically, when used, the solvent can be present in an amount up to 1,000 wt. %, based on the weight of the linear aldehyde. Alternatively, the linear aldehyde and the dehydroformylation catalyst system can be contacted in the presence of a solvent in an amount up 750 wt. %, up to 500 wt. %, up to 250 wt. %, up to 200 wt. %, up to 150 wt. %, or up to 100 wt. %. When a solvent is utilized, the minimum amount of solvent utilized can be at least 5 wt. %, at least 10 wt. %, at least 25 wt. %, at least 50 wt. %, or at least 75 wt. %, based on the weight of the linear aldehyde. Generally, the amount of solvent which can be utilized can range from any minimum amount of solvent disclosed herein to any maximum amount of solvent disclosed herein. In some non-limiting embodiments, the linear aldehyde and the dehydroformylation catalyst system can be contacted in the presence of a solvent in an amount of from 5 wt. % to 1,000 wt. %, from 10 wt. % to 750 wt. %, from 25 wt. % to 500 wt. %, from 50 wt. % to 250 wt. %, from 50 wt. % to 150 wt. %, or from 75 wt. % to 125 wt. %, based on the weight of the linear aldehyde.

As described herein, the linear aldehyde and the dehydroformylation catalyst system can be contacted in the presence of a solvent. In one embodiment, the solvent can comprise, consist essentially of, or consist of, a polar solvent, while in another embodiment, the solvent can comprise, consist essentially of, or consist of, a ketone, an alcohol, an ether, or any combination thereof. Hence, mixtures and/or combinations of solvents can be utilized in the dehydroformylation step and the normal alpha olefin synthesis processes disclosed herein.

In an embodiment, the solvent employed in the dehydroformylation step can comprise, consist essentially of, or consist of, a ketone, an alcohol, an ether, or any combination thereof; alternatively, a ketone; alternatively, an alcohol; or alternatively, an ether. Suitable ketones, alcohols, or ethers include $C_2$ to $C_{20}$ ketones, alcohols, or ethers; alternatively, $C_2$ to $C_{10}$ ketones, alcohols, or ethers; or alternatively, $C_2$ to $C_5$ ketones, alcohols, or ethers. Non-limiting examples of suitable ketone solvents can include acetone, ethyl methyl ketone, or any combination thereof. Non-limiting examples of suitable alcohol solvents can include methanol, ethanol, propanol, isopropanol, n-butanol, isobutanol, pentanol, hexanol, heptanol, octanol, benzyl alcohol, phenol, cyclohexanol, or any combination thereof. Suitable ether solvents can be cyclic or acyclic, non-limiting examples of which can include dimethyl ether, diethyl ether, methyl ethyl ether, dibutylether, monoethers or diethers of glycols (e.g., a dimethyl glycol ether), glyme, diglyme, tetraglyme, furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group.

Consistent with embodiments of this invention, the linear internal olefin product of metathesis step (i), and/or the linear aldehyde product of hydroformylation step (ii), and/or the second normal alpha olefin product of dehydroformylation step (iii), can be isolated or separated from reaction by-products, residual reactants, catalyst systems components, and the like. As would be recognized by those skilled in the art, the linear internal olefin product of metathesis step (i), and/or the linear aldehyde product of hydroformylation step (ii), and/or the second normal alpha olefin product of dehydroformylation step (iii), can be isolated or separated using any suitable technique, such as filtration, evaporation, distillation, or any combination of two or more of these techniques.

In another embodiment of this invention, a process for producing a normal alpha olefin is provided, and in this embodiment, the process can comprise (or consist essentially of, or consist of) (a) contacting a linear internal olefin having the structure $CH_3(CH_2)_pHC=CH(CH_2)_qCH_3$ with a hydroformylation catalyst system, carbon monoxide, and hydrogen to form a linear aldehyde having the formula $CH_3(CH_2)_{p+q+3}C(=O)H$; and (b) contacting the linear aldehyde with a dehydroformylation catalyst system comprising i) a transition metal compound, a diphosphine, and a carboxylic acid or carboxylic acid derivative, or ii) a diphosphine transition metal compound complex and a carboxylic acid or carboxylic acid derivative, to form a normal alpha olefin having the structure $CH_3(CH_2)_{p+q+1}HC=CH_2$. In this process, p and q can be integers that independently can range from 0 to 15. In this process, p and q can be the same or different; alternatively, the same; or alternatively, different. Generally, the features of this process (e.g., the linear internal olefin, the hydroformylation catalyst system, the linear aldehyde, the dehydroformylation catalyst system, the normal alpha olefin, and the conditions under which each of the steps are conducted, among other features) are independently described herein and these features can be combined in any combination to further describe the disclosed normal alpha olefin synthesis process. Moreover, additional process steps can be performed before, during, and/or after any of the steps of any of the processes disclosed herein, unless stated otherwise.

For instance, the internal olefin having the formula $CH_3(CH_2)_pHC=CH(CH_2)_qCH_3$ can be produced by any method known to those having ordinary skill in the art. In an embodiment, the linear internal olefin having the structure $CH_3(CH_2)_pHC=CH(CH_2)_qCH_3$ can be produced by the metathesis of an alpha olefin having the formula $CH_3(CH_2)_pHC=CH_2$ and an alpha olefin having the formula $CH_3(CH_2)_qHC=CH_2$: e.g., the process for producing a normal alpha olefin can further comprise a step of contacting a normal alpha olefin having the structure $CH_3(CH_2)_pHC=CH_2$, a normal alpha olefin having the formula $CH_3(CH_2)_qHC=CH_2$, and a metathesis catalyst system to form the linear internal olefin having the structure $CH_3(CH_2)_pHC=CH(CH_2)_qCH_3$. In another embodiment, the linear internal olefin having the structure $CH_3(CH_2)_pHC=CH(CH_2)_qCH_3$ can be produced by the dehydrogenation of a linear alkane having the formula $CH_3(CH_2)_{p+q+2}CH_3$.

In this process, step (a) is often referred to as the hydroformylation step, and step (a) can have any of the features and attributes (e.g., the hydroformylation catalyst system) as that described herein for hydroformylation step (ii). Likewise, step (b) is often referred to as the dehydroformylation step, and step (b) can have any of the feature or attributes (e.g., the dehydroformylation catalyst system, the aldehyde group acceptor) as that described herein for dehydroformylation step (iii). Moreover, if the process further includes a metathesis step for producing the linear internal olefin having the structure $CH_3(CH_2)_pHC=CH(CH_2)_qCH_3$, the metathesis step can have any of the features or attributes (e.g., the metathesis catalyst system and metathesis conditions, among others) as described herein for metathesis step (i).

In this normal alpha olefin synthesis process, p and q independently can be integers that range from 0 to 15. In one embodiment consistent with this invention, p and q independently can be an integer from 0 to 10, while in another embodiment, p and q independently can be an integer from 0 to 7. Yet, in another embodiment, p and q independently can be an integer from 1 to 7, and in still another embodiment, p and q independently can be an integer from 1 to 5. For example, p and q independently can be equal to 1, equal to 2, equal to 3, or equal to 4.

The normal alpha olefin produced in this process, having the structure $CH_3(CH_2)_{p+q+1}HC=CH_2$, is not particularly limited. However, in one embodiment of this invention, the normal alpha olefin can comprise, consist essentially of, or consist of, 1-butene, 1-hexene, 1-octene, 1-decene, 1-dodecene, 1-tetradecene, 1-hexadecene, 1-octadecene, or any combination thereof; alternatively, 1-hexene, 1-octene, 1-decene, 1-dodecene, 1-tetradecene, or any combination thereof; or alternatively, 1-hexene, 1-octene, 1-decene, or any combination thereof. In another embodiment, the normal alpha olefin can comprise, consist essentially of, or consist of, 1-butene; alternatively, 1-hexene; alternatively, 1-octene; alternatively, 1-decene; alternatively, 1-dodecene; alternatively, 1-tetradecene; alternatively, 1-hexadecene; or alternatively, 1-octadecene. In yet another embodiment, the normal alpha olefin can comprise, consist essentially of, or consist of, 1-hexene, 1-octene, 1-decene, or any combination thereof.

The integer p, the integer q, and the normal alpha olefin are described herein and their features can be utilized without limitation to further describe the normal alpha olefin synthesis process disclosed herein. Other suitable values for the integer p and the integer q, and selections for the normal alpha olefin, are readily apparent from this disclosure.

In an embodiment, wherein the linear internal olefin is produce via metathesis, 1) the normal alpha olefin having the structure $CH_3(CH_2)_pHC=CH_2$ can be propene, 2) the normal alpha olefin having the formula $CH_3(CH_2)_qHC=CH_2$ can be pentene, 3) the linear internal olefin can be a linear internal butene, a linear internal hexene, a linear internal octene, or any combination thereof, and 4) the normal alpha olefin having the structure $CH_3(CH_2)_{p+q+1}HC=CH_2$ can be 1-butene, 1-hexene, 1-octene, or any combination thereof; or alternatively, 1) the normal alpha olefin having the structure $CH_3(CH_2)_pHC=CH_2$ can be propene, 2) the normal alpha olefin having the formula $CH_3(CH_2)_qHC=CH_2$ can be heptene, 3) the linear internal olefin can be a linear internal butene, a linear internal octene, a linear internal dodecene, or any combination thereof, and 4) the normal alpha olefin having the structure $CH_3(CH_2)_{p+q+1}HC=CH_2$ can be 1-butene, 1-octene, 1-dodecene, or any combination thereof. In some embodiments, wherein the linear internal olefin is produce via metathesis, 1) the normal alpha olefin having the structure $CH_3(CH_2)_pHC=CH_2$ can be butene, 2) the normal alpha olefin having the formula $CH_3(CH_2)_qHC=CH_2$ can be hexene, 3) the linear internal olefin can be a linear internal hexene, a linear internal octene, a linear internal decene, or any combination thereof, and 4) the normal alpha olefin having the structure $CH_3(CH_2)_{p+q+1}HC=CH_2$ can be 1-hexene, 1-octene, 1-decene, or any combination thereof; or alternatively, 1) the normal alpha olefin having the structure $CH_3(CH_2)_pHC=CH_2$ can be butene, 2) the normal alpha olefin having the formula $CH_3(CH_2)_qHC=CH_2$ can be octene, 3) the linear internal olefin can be a linear internal hexene, a linear internal decene, a linear internal tetradecene, or any combination thereof, and 4) the normal alpha olefin having the structure $CH_3(CH_2)_{p+q+1}HC=CH_2$ can be 1-hexene, 1-decene, 1-tetradecene, or any combination thereof. In other embodiments, wherein the linear internal olefin is produce via metathesis, 1) the normal alpha olefin having the structure $CH_3(CH_2)_pHC=CH_2$ can be pentene, 2) the normal alpha olefin having the formula $CH_3(CH_2)_qHC=CH_2$ can be heptene, 3) the linear internal olefin can be a linear internal octene, a linear internal decene, a linear internal dodecene, or any combination thereof, and 4) the normal alpha olefin having the structure $CH_3(CH_2)_{p+q+1}HC=CH_2$ can be 1-octene, 1-decene, 1-dodecene, or any combination thereof. Other combinations of 1) a normal alpha olefin having the structure $CH_3(CH_2)_pHC=CH_2$, 2) a normal alpha olefin having the formula $CH_3(CH_2)_qHC=CH_2$, 3) a linear internal olefin, and 4) a normal alpha olefin having the structure $CH_3(CH_2)_{p+q+1}HC=CH_2$ are readily apparent from this disclosure.

EXAMPLES

The invention is further illustrated by the following constructive examples, which are not to be construed in any way as imposing limitations to the scope of this invention. Various other aspects, embodiments, modifications, and equivalents thereof which, after reading the description herein, can suggest themselves to one of ordinary skill in the art without departing from the spirit of the present invention or the scope of the appended claims.

Constructive Example 1

Constructive Example 1 demonstrates the conversion of 1-hexene to 1-decene via a metathesis (homogeneous), isomerization-hydroformylation (un-ligated), and dehydroformylation pathway as shown in the synthesis scheme below (where n=3).

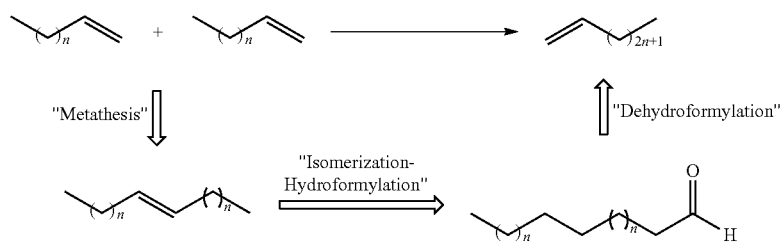

or any combination thereof, and 4) the normal alpha olefin having the structure $CH_3(CH_2)_{p+q+1}HC=CH_2$ can be The reaction scheme for the homogeneous metathesis step is shown below.

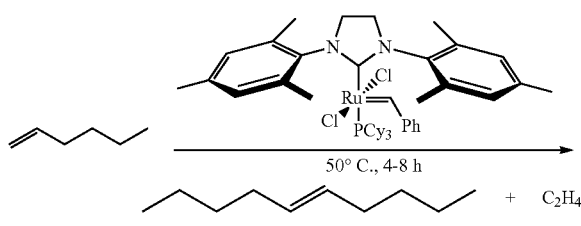

The metathesis step can be performed as follows. In a drybox under an N₂ atmosphere, a 500 mL round bottom flask with a magnetic stir bar is charged with 1-hexene (250 mL, 168 g, ~2 mol). The flask is placed in an aluminum block on a temperature controlled heating plate at ~50° C. and allowed to equilibrate temperature. To this stirring solution, a Grubbs 2$^{nd}$ Generation Catalyst (dichloro [1,3-bis(2,4,6-trimethylphenyl)-2-imidazolidinylidene] (benzylidene) (tricyclohexyl-phosphine) ruthenium(II), 4.2 mg, 4.9 µmol) is added to initiate the reaction. Reaction progress can be monitored by taking aliquot samples and analyzing them by GC-FID for reaction equilibrium, which typically takes 4-8 hr. Any produced ethylene is allowed to bubble and leave the flask as it is not capped in the glovebox. Upon completion of the reaction, the solution is cooled, filtered, and the reaction contents distilled to isolate 5-decene. The reaction yield is ~40-50% 5-decene by fractional distillation.

The reaction scheme for the isomerization-hydroformylation (un-ligated) step is shown below.

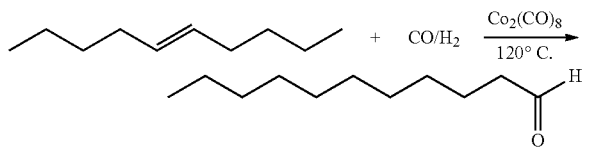

The isomerization-hydroformylation step can be performed as follows. A 5 L continuously stirred autoclave is charged with 190 g (1 mol) of 5-decene in 3.8 L of benzene and 4.27 g (0.0125 mol) of recently sublimed Co₂(CO)₈. The decene:cobalt molar ratio is maintained at ~40:1. The autoclave is pressurized with 3000 psig of a 1:1 mix of Syn-Gas mixture (CO:H₂) that is fed on demand and is heated at 120° C. until the reaction reaches 40-60% conversion, as monitored by aliquot sampling and GC-FID analysis. GC-FID reveals that, upon analysis of the reaction, greater than 50% of the internal olefin is converted to the primary aldehyde, 1-undecanal. The remainder of the product is a mixture of the various internal aldehydes declining in yield from the primary position. The products then can be individually isolated by fractional distillation to yield 90+% pure 1-undecanal.

The reaction scheme for the dehydroformylation step is shown below.

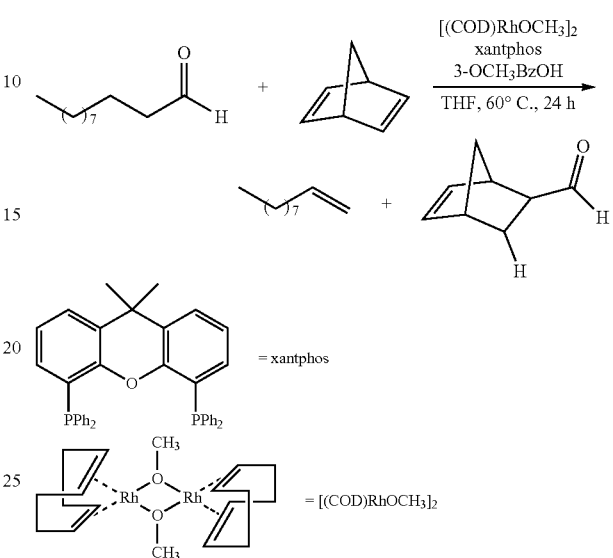

The dehydroformylation step to produce 1-decene can be performed as follows. In a drybox under an N₂ atmosphere, a 500 mL round bottom flask with a magnetic stir bar is charged with [(COD)RhOCH₃]₂ (2.72 g, 5 mmol), xantphos (5.79 g, 10 mmol), 3-methoxybenzoate (1.52 g, 10 mmol), 1-undecanal (170 g, 1 mol), and 250 mL (~3 mol) of THF. Norbornadiene (111 g, 1.2 mol) is then added last to the reaction mixture. The flask is placed in an aluminum block on a temperature controlled heating plate for 24 hr at 60° C. Reaction progress is monitored by taking aliquot samples and analyzing via GC-FID. Upon completion of the reaction, the reaction mixture is cooled, filtered, and the reaction product is distilled to isolate decene by fractional distillation. Product yield is 90+% decenes in a 95:5 ratio of 1-decene:2-decene, as determined by GC-FID.

Constructive Example 2

Constructive Example 2 demonstrates the conversion of 1-hexene to 1-decene via a metathesis (heterogeneous), isomerization-hydroformylation (ligated), and dehydroformylation pathway as shown in the synthesis scheme below (where n=3).

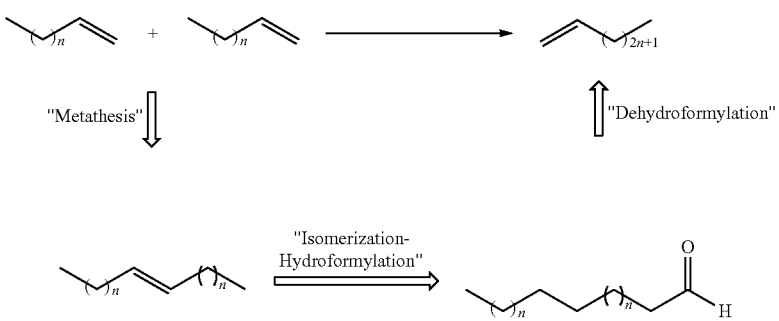

The reaction scheme for the heterogeneous metathesis step is shown below.

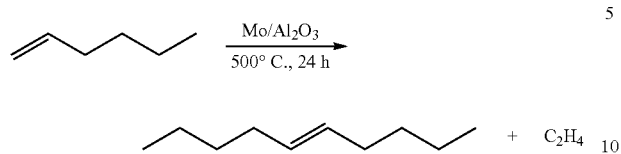

The metathesis step can be performed as follows. A 4-inch I.D. by 5-foot long stainless steel pipe is heated electrically for controlling reactor temperature and for catalyst activation/regeneration. The reactor contains 8.2 kg of molybdenum oxide-on-alumina catalyst (1.3% $MoO_3$, 0.07% $SiO_2$) from Nalco Chemical Company, consisting of ⅛" extrudate pellets treated with 1.5 wt. % KOH. The catalyst is regenerated by "burning off" polymer and hydrocarbons, and holding the catalyst for 6 hr at 565° C. under air. The catalyst temperature is then reduced and the atmosphere changed to $N_2$. 1-hexene is distilled prior to use and charged to an olefin feed vessel. From the feed vessel, the 1-hexene is pumped at constant rate upflow through the catalyst bed. Reaction conditions are typically 87-110° C., at 20 psig pressure, with an LHSV of 0.5. The product then can be flowed into a product hold vessel, where ethylene is allowed to be flashed overhead. The crude product is then sent to a kettle bottom of a distillation column and distilled until the concentration of 5-decene in the kettle bottom reaches ~80%. At this point, approximately, 20 L of crude kettle product is obtained. The crude kettle product, approximately 73 kg, is loaded into the kettle of a 2" stainless steel distillation column with ¼" Octapac and distilled with 5-decene coming as the last cut at 86-89° C. at 50 mm Hg to yield approximately 41 kg of 5-decene with the following estimated specifications:

| | |
|---|---|
| Purity (wt. %) | 99.6 |
| cis 5-decene (wt. %) | 18.1 |
| trans 5-decene (wt. %) | 81.5 |
| Specific gravity (20/20° C.) | 0.742 |
| Refractive index ($N_D^{20}$) | 1.428 |
| Freezing point (° C.) | −75.8 |
| Boiling point (° C.) | 169.8 |

The reaction scheme for the isomerization-hydroformylation (ligated) step is shown below.

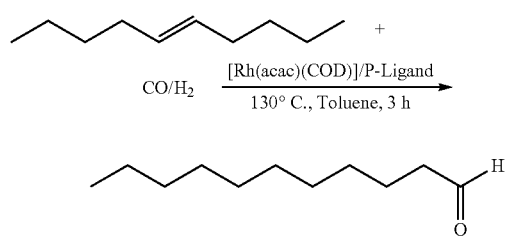

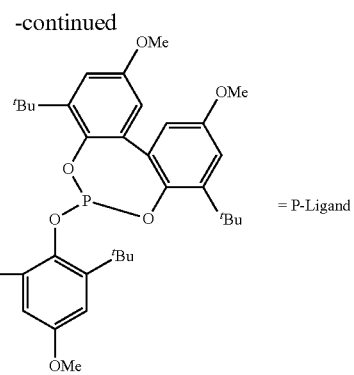

The isomerization-hydroformylation step can be performed as follows. A 1 L continuously stirred autoclave is charged with 600 mL of a 1.68 M solution of 5-decene (~190 g, 1 mol) in toluene, 0.2 g (0.63 mmol) of [Rh(acac)(COD)], and 5.8 g (6.4 mmol) of 3-aryloxy-1,3,2-dioxaphosphine-4-ones ligand, P-Ligand. The autoclave is pressurized with 300 psig of a 1:1 mix of syngas mixture ($CO:H_2$) that is fed on demand and is heated at 130° C. for 3 hr. GC-FID reveals that, upon analysis of the reaction, greater than 65% of the internal olefin is converted to the primary aldehyde, 1-undecanal. The remainder of the product is a mixture of the various internal aldehydes declining in yield from the primary position. The products then can be individually isolated by fractional distillation to yield 90+% pure 1-undecanal.

The reaction scheme for the dehydroformylation step is shown below.

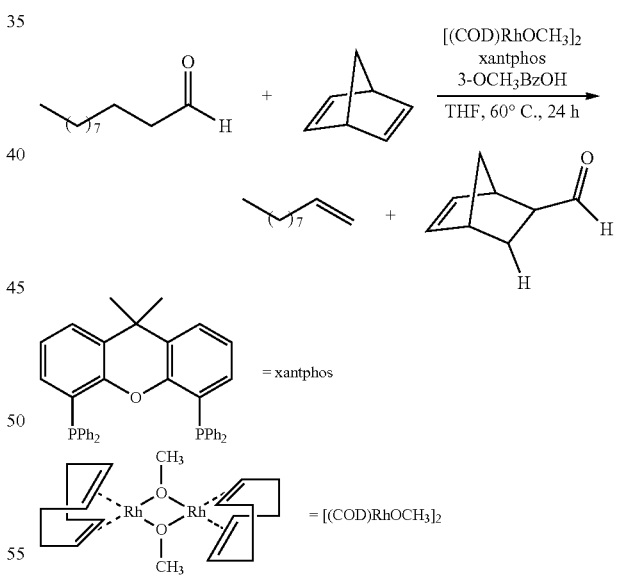

The dehydroformylation step to produce 1-decene can be performed as follows. In a drybox under an $N_2$ atmosphere, a 500 mL round bottom flask with a magnetic stir bar is charged with [(COD)RhOCH$_3$]$_2$ (2.72 g, 5 mmol), xantphos (5.79 g, 10 mmol), 3-methoxybenzoate (1.52 g, 10 mmol), 1-undecanal (170 g, 1 mol), and 250 mL (~3 mol) of THF. Norbornadiene (111 g, 1.2 mol) is then added last to the reaction mixture. The flask is placed in an aluminum block on a temperature controlled heating plate for 24 hr at 60° C. Reaction progress is monitored by taking aliquot samples and analyzing via GC-FID. Upon completion of the reaction, the reaction mixture is cooled, filtered, and the reaction product is distilled to isolate decene by fractional distillation. Product yield is 90+% decenes in a 95:5 ratio of 1-decene:2-decene, as determined by GC-FID.

The invention is described herein with reference to numerous aspects and embodiments, and specific examples. Many variations will suggest themselves to those skilled in the art in light of the detailed description. All such obvious variations are within the full intended scope of the appended claims. Other embodiments of the invention can include, but are not limited to, the following (embodiments are described as "comprising" but, alternatively, can "consist essentially of" or "consist of"):

Embodiment 1

A process comprising:
(i) contacting a first normal alpha olefin having the structure $CH_3(CH_2)_nHC\!=\!CH_2$ and a metathesis catalyst system to form a linear internal olefin having the structure $CH_3(CH_2)_nHC\!=\!CH(CH_2)_nCH_3$;
(ii) contacting the linear internal olefin with a hydroformylation catalyst system, carbon monoxide, and hydrogen to form a linear aldehyde having the formula $CH_3(CH_2)_{2n+3}C(\!=\!O)H$; and
(iii) contacting the linear aldehyde with a dehydroformylation catalyst system comprising i) a transition metal compound, a diphosphine, and a carboxylic acid or carboxylic acid derivative, or ii) a diphosphine transition metal compound complex and a carboxylic acid or carboxylic acid derivative, to form a second normal alpha olefin having the structure $CH_3(CH_2)_{2n+1}HC\!=\!CH_2$;
wherein n is an integer from 0 to 15.

Embodiment 2

The process defined in embodiment 1, wherein n is an integer from 0 to 10.

Embodiment 3

The process defined in embodiment 1, wherein n is an integer from 1 to 7.

Embodiment 4

The process defined in embodiment 1, wherein the first normal alpha olefin comprises propylene, 1-butene, 1-pentene, 1-hexene, 1-heptene, 1-octene, 1-nonene, 1-decene, 1-dodecene, 1-tetradecene, 1-hexadecene, 1-octadecene, or any combination thereof.

Embodiment 5

The process defined in embodiment 1, wherein the first normal alpha olefin comprises 1-butene, 1-pentene, 1-hexene, 1-heptene, 1-octene, or any combination thereof.

Embodiment 6

The process defined in embodiment 1, wherein the first normal alpha olefin comprises 1-butene, and the second normal alpha olefin comprises 1-hexene.

Embodiment 7

The process defined in embodiment 1, wherein the first normal alpha olefin comprises 1-pentene, and the second normal alpha olefin comprises 1-octene.

Embodiment 8

The process defined in embodiment 1, wherein the first normal alpha olefin comprises 1-hexene, and the second normal alpha olefin comprises 1-decene.

Embodiment 9

The process defined in any one of the preceding embodiments, wherein the metathesis catalyst system is a metal oxide based metathesis catalyst system, a metal halide based metathesis catalyst system, a metal carbene based metathesis catalyst system, or any combination thereof.

Embodiment 10

The process defined in embodiment 9, wherein the metal oxide based metathesis catalyst system comprises cobalt oxide, molybdenum oxide, tungsten oxide, rhenium oxide, or any combination thereof.

Embodiment 11

The process defined in embodiment 10, wherein the metal oxide based metathesis catalyst system further comprises a support and/or a metal alkyl activator.

Embodiment 12

The process defined in embodiment 9, wherein the metal halide based metathesis catalyst system comprises a halide of tungsten, a halide of molybdenum, or any combination thereof.

Embodiment 13

The process defined in embodiment 12, wherein the metal halide based metathesis catalyst system further comprises a metal alkyl activator and/or oxygen or an alcohol.

Embodiment 14

The process defined in embodiment 9, wherein the metal carbene based metathesis catalyst system comprises tungsten, tantalum, osmium, molybdenum, ruthenium, or any combination thereof.

Embodiment 15

The process defined in embodiment 14, wherein the metal carbene based metathesis catalyst system further comprises a support.

Embodiment 16

A process comprising:
(a) contacting a linear internal olefin having the structure $CH_3(CH_2)_pHC\!=\!CH(CH_2)_qCH_3$ with a hydroformylation catalyst system, carbon monoxide, and hydrogen to form a linear aldehyde having the formula $CH_3(CH_2)_{p+q+3}C(\!=\!O)H$; and (b) contacting the linear aldehyde with a dehydroformylation catalyst system comprising i) a transition metal compound, a diphosphine, and a carboxylic acid or carboxylic acid derivative, or ii) a diphosphine transition metal compound complex and a carboxylic acid or carboxylic acid derivative, to form a normal alpha olefin having the structure $CH_3(CH_2)_{p+q+1}HC = CH_2$;

wherein p and q independently are an integer from 0 to 15.

Embodiment 17

The process defined in embodiment 16, wherein p and q independently are an integer from 0 to 10.

Embodiment 18

The process defined in embodiment 16, wherein p and q independently are an integer from 1 to 7.

Embodiment 19

The process defined in embodiment 16, wherein the normal alpha olefin comprises 1-butene, 1-hexene, 1-octene, 1-decene, 1-dodecene, 1-tetradecene, 1-hexadecene, 1-octadecene, or any combination thereof.

Embodiment 20

The process defined in embodiment 16, wherein the normal alpha olefin comprises 1-hexene.

Embodiment 21

The process defined in embodiment 16, wherein the normal alpha olefin comprises 1-octene.

Embodiment 22

The process defined in embodiment 16, wherein the normal alpha olefin comprises 1-decene.

Embodiment 23

The process defined in any one of embodiments 1-22, wherein the hydroformylation catalyst system comprises a rhodium compound, a cobalt compound, a ruthenium compound, an iridium compound, a platinum compound, a palladium compound, an iron compound, or any combination thereof.

Embodiment 24

The process defined in any one of embodiments 1-22, wherein the hydroformylation catalyst is a hydroformylation catalyst system comprising a cobalt compound, a hydroformylation catalyst comprising a rhodium compound, or any combination thereof.

Embodiment 25

The process defined in any one of the preceding embodiments, wherein step (iii) (or step (b)) comprises contacting the linear aldehyde with 1) the dehydroformylation catalyst system comprising i) the transition metal compound, the diphosphine, and the carboxylic acid or carboxylic acid derivative, or ii) the diphosphine transition metal compound complex and the carboxylic acid or carboxylic acid derivative, and 2) an aldehyde group acceptor (e.g., an acceptor olefin) to form the second normal alpha olefin (or the normal alpha olefin).

Embodiment 26

The process defined in embodiment 25, wherein the aldehyde group acceptor (e.g., acceptor olefin) comprises a mono-olefin compound (e.g., ethylene, norbornene), a di-olefin compound (e.g., cyclooctadiene, norbornadiene), a tri-olefin compound (e.g., cyclododecatriene), or any combination thereof.

Embodiment 27

The process defined in embodiment 25 or 26, wherein the aldehyde group acceptor (e.g., acceptor olefin) is an aliphatic hydrocarbon compound.

Embodiment 28

The process defined in any one of embodiments 25-27, wherein the aldehyde group acceptor (e.g., acceptor olefin) is a cyclic compound.

Embodiment 29

The process defined in embodiment 25, wherein the aldehyde group acceptor comprises an unsaturated triglyceride or an unsaturated natural source oil, e.g., soybean oil, corn oil, castor bean oil, canola oil, or any combination thereof.

Embodiment 30

The process defined in any one of the preceding embodiments, wherein the linear aldehyde and the dehydroformylation catalyst system are contacted in the presence of a polar solvent (e.g., THF, dioxane).

Embodiment 31

The process defined in any one of the preceding embodiments, wherein the dehydroformylation catalyst system comprises a rhodium compound.

Embodiment 32

The process defined in embodiment 31, wherein the rhodium compound of the dehydroformylation catalyst system comprises an olefin rhodium alkoxide complex.

Embodiment 33

The process defined in embodiment 31, wherein the rhodium compound of the dehydroformylation catalyst system comprises a cyclodiene rhodium alkoxide complex.

Embodiment 34

The process defined in any one of the preceding embodiments, wherein the diphosphine or the diphosphine of the diphosphine transition metal compound complex has structure (I):

$$\begin{array}{c} \phantom{L^1}\diagup PR_2 \\ L^1 \\ \phantom{L^1}\diagdown PR_2; \end{array} \quad (I)$$

wherein:

L$^1$ is a linking group; and each R independently is H or a $C_1$ to $C_{18}$ hydrocarbyl group.

Embodiment 35

The process defined in any one of embodiment 1-33, wherein the diphosphine or the diphosphine of the diphosphine transition metal compound complex comprises a 1,6-bisphosphinylhexane, a substituted 1,6-bisphosphinylhexane, a (1,3-phenylenedi-1,1-ethanediyl)bis(phosphine), a substituted (1,3-phenylenedi-1,1-ethanediyl)bis(phosphine), a 1,8-anthracenediylbis(phosphine), a substituted 1,8-anthracenediylbis(phosphine), a 1,8-tetradecahydroanthracenediylbis(phosphine), or a substituted 1,8-tetradecahydroanthracenediylbis(phosphine), a (methylenedi-2,1-phenylene)bis(phosphine), a substituted (methylenedi-2,1-phenylene)bis(phosphine), a 9H-xanthene-4,5-diylbis(phosphine), or a substituted 9H-xanthene-4,5-diylbis(phosphine).

Embodiment 36

The process defined in any one of embodiments 1-33, wherein the diphosphine or the diphosphine of the transition metal compound complex has any one of the following structures:

wherein:

Ph is a phenyl group; and each R independently is H or a $C_1$ to $C_{18}$ hydrocarbyl group.

Embodiment 37

The process defined in any one of embodiments 1-36, wherein the carboxylic acid or carboxylic acid derivative comprises benzoic acid or a substituted benzoic acid, or a salt or ester of benzoic acid or a substituted benzoic acid.

Embodiment 38

The process defined in any one of embodiments 1-37, wherein the second normal alpha olefin in step (iii) (or the normal alpha olefin in step (b)) is formed at a temperature from 0° C. to 150° C.

Embodiment 39

The process defined in any one of embodiments 25-38, wherein the molar ratio of the aldehyde group acceptor (e.g., acceptor olefin) to the linear aldehyde is in a range from 0.2:1 to 1,000:1.

Embodiment 40

The process defined in any one of the preceding embodiments, wherein the molar ratio of the linear aldehyde to the transition metal of the transition metal compound or the diphosphine transition metal compound complex is in a range from 0.00001:1 to 0.05:1.

Embodiment 41

The process defined in any one of the preceding embodiments, wherein the molar ratio of the transition metal of the transition metal compound to the diphosphine is in a range from 0.8:1 to 5:1.

Embodiment 42

The process defined in any one of the preceding embodiments, wherein the molar ratio of the transition metal of the transition metal compound or the diphosphine transition metal compound complex to the carboxylic acid or carboxylic acid derivative is in a range from 0.8:1 to 5:1.

I claim:

1. A process comprising:
    (i) contacting a first normal alpha olefin having the structure $CH_3(CH_2)_n HC=CH_2$ and a metathesis catalyst system to form a linear internal olefin having the structure $CH_3(CH_2)_n HC=CH(CH_2)_n CH_3$;
    (ii) contacting the linear internal olefin with a hydroformylation catalyst system, carbon monoxide, and hydrogen to form a linear aldehyde having the formula $CH_3(CH_2)_{2n+3}C(=O)H$; and
    (iii) contacting the linear aldehyde with a dehydroformylation catalyst system comprising i) a transition metal compound, a diphosphine, and a carboxylic acid or carboxylic acid derivative, or ii) a diphosphine transition metal compound complex and a carboxylic acid or carboxylic acid derivative, to form a second normal alpha olefin having the structure $CH_3(CH_2)_{2n+1}HC=CH_2$;
    wherein n is an integer from 0 to 15.

2. The process of claim 1, wherein n is an integer from 1 to 7.

3. The process of claim 1, wherein the first normal alpha olefin comprises 1-butene, 1-pentene, 1-hexene, 1-heptene, 1-octene, or any combination thereof.

4. The process of claim 1, wherein the first normal alpha olefin comprises 1-hexene, and the second normal alpha olefin comprises 1-decene.

5. The process of claim 1, wherein step (iii) comprises contacting the linear aldehyde with 1) the dehydroformylation catalyst system comprising i) the transition metal compound, the diphosphine, and the carboxylic acid or carboxylic acid derivative, or ii) the diphosphine transition metal compound complex and the carboxylic acid or carboxylic acid derivative, and 2) an aldehyde group acceptor to form the second normal alpha olefin.

6. The process of claim 5, wherein the aldehyde group acceptor comprises an aliphatic mono-olefin hydrocarbon, an aliphatic di-olefin hydrocarbon, an aliphatic tri-olefin hydrocarbon, or any combination thereof.

7. The process of claim 5, wherein a molar ratio of the aldehyde group acceptor to the linear aldehyde is in a range from 0.2:1 to 1,000:1.

8. The process of claim 5, wherein n is an integer from 1 to 7.

9. The process of claim 1, wherein the dehydroformylation catalyst system comprises a rhodium compound.

10. The process of claim 1, wherein:
the diphosphine or the diphosphine of the diphosphine transition metal compound complex comprises a 1,6-bisphosphinylhexane, a substituted 1,6-bisphosphinylhexane, a (1,3-phenylenedi-1,1-ethanediyl)bis(phosphine), a substituted (1,3-phenylenedi-1,1-ethanediyl)bis(phosphine), a 1,8-anthracenediylbis(phosphine), a substituted 1,8-anthracenediylbis(phosphine), a 1,8-tetradecahydroanthracenediylbis(phosphine), or a substituted 1,8-tetradecahydroanthracenediylbis(phosphine), a (methylenedi-2,1-phenylene)bis(phosphine), a substituted (methylenedi-2,1-phenylene)bis(phosphine), a 9H-xanthene-4,5-diylbis(phosphine), or a substituted 9H-xanthene-4,5-diylbis(phosphine); and
the carboxylic acid or carboxylic acid derivative comprises benzoic acid or a substituted benzoic acid, or a salt or ester of benzoic acid or of a substituted benzoic acid.

11. The process of claim 1, wherein
a molar ratio of the linear aldehyde to the transition metal of the transition metal compound or the diphosphine transition metal compound complex is in a range from 0.00001:1 to 0.05:1; and
a molar ratio of the transition metal of the transition metal compound or the diphosphine transition metal compound complex to the carboxylic acid or carboxylic acid derivative is in a range from 0.8:1 to 5:1.

12. The process of claim 1, wherein the metathesis catalyst system is a metal oxide based metathesis catalyst system, a metal halide based metathesis catalyst system, a metal carbene based metathesis catalyst system, or any combination thereof.

13. The process of claim 1, wherein the hydroformylation catalyst system comprises a rhodium compound, a cobalt compound, a ruthenium compound, an iridium compound, a platinum compound, a palladium compound, an iron compound, or any combination thereof.

14. A process comprising:
(a) contacting a linear internal olefin having the structure $CH_3(CH_2)_pHC=CH(CH_2)_qCH_3$ with a hydroformylation catalyst system, carbon monoxide, and hydrogen to form a linear aldehyde having the formula $CH_3(CH_2)_{p+q+3}C(=O)H$; and (b) contacting the linear aldehyde with a dehydroformylation catalyst system comprising i) a transition metal compound, a diphosphine, and a carboxylic acid or carboxylic acid derivative, or ii) a diphosphine transition metal compound complex and a carboxylic acid or carboxylic acid derivative, to form a normal alpha olefin having the structure $CH_3(CH_2)_{p+q+1}HC=CH_2$;
wherein p and q independently are an integer from 0 to 15.

15. The process of claim 14, wherein p and q independently are an integer from 1 to 7.

16. The process of claim 15, wherein step (b) comprises contacting the linear aldehyde with 1) the dehydroformylation catalyst system comprising i) the transition metal compound, the diphosphine, and the carboxylic acid or carboxylic acid derivative, or ii) the diphosphine transition metal compound complex and the carboxylic acid or carboxylic acid derivative, and 2) an aldehyde group acceptor to form the normal alpha olefin.

17. The process of claim 14, wherein the normal alpha olefin comprises 1-butene, 1-hexene, 1-octene, 1-decene, 1-dodecene, 1-tetradecene, 1-hexadecene, 1-octadecene, or any combination thereof.

18. The process of claim 17, wherein the diphosphine or the diphosphine of the transition metal compound complex has any one of the following structures:

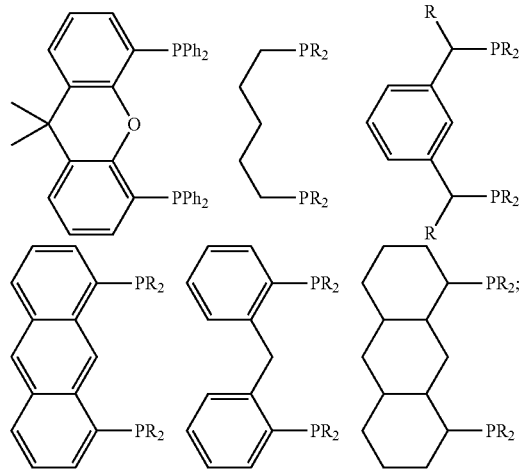

wherein:
Ph is a phenyl group; and
each R independently is H or a $C_1$ to $C_{18}$ hydrocarbyl group.

19. The process of claim 14, wherein the linear aldehyde and the dehydroformylation catalyst system are contacted in the presence of a polar solvent.

20. The process of claim 19, wherein the normal alpha olefin comprises 1-hexene, 1-octene, 1-decene, or any combination thereof.

* * * * *